US009848820B2

(12) United States Patent
Chen et al.

(10) Patent No.: US 9,848,820 B2
(45) Date of Patent: Dec. 26, 2017

(54) APNEA ANALYSIS SYSTEM AND METHOD

(71) Applicant: Covidien LP, Mansfield, MA (US)

(72) Inventors: Bo Chen, Louisville, CO (US);
Michael L. Mestek, Superior, CO (US);
Ron J. Kadlec, Longmont, CO (US);
Niranjan Maharajh, Broomfield, CO (US); Mark E. Kolnsberg, Beverly, MA (US); Corinne H. Johnson, Denver, CO (US); James P. Ochs, Seattle, WA (US); Paul Stanley Addison, Edinburgh (GB); James N. Watson, Edinburgh (GB)

( * ) Notice: Subject to any disclaimer, the term of this patent is extended or adjusted under 35 U.S.C. 154(b) by 32 days.

(21) Appl. No.: 14/590,609

(22) Filed: Jan. 6, 2015

(65) Prior Publication Data

US 2015/0190088 A1 Jul. 9, 2015

Related U.S. Application Data

(60) Provisional application No. 61/924,440, filed on Jan. 7, 2014.

(51) Int. Cl.
*A61B 5/00* (2006.01)
*A61B 5/0205* (2006.01)
(Continued)

(52) U.S. Cl.
CPC ........ *A61B 5/4818* (2013.01); *A61B 5/02055* (2013.01); *A61B 5/02416* (2013.01);
(Continued)

(58) Field of Classification Search
CPC ............................. A61B 5/4818; A61B 5/0826
See application file for complete search history.

(56) References Cited

U.S. PATENT DOCUMENTS 5,188,108 A 2/1993 Seeker
5,285,783 A 2/1994 Seeker
(Continued)

FOREIGN PATENT DOCUMENTS

EP 0072601 A1 2/1983
EP 1344488 A2 9/2004
(Continued)

OTHER PUBLICATIONS

PCT Notification of Transmittal of the International Search Report and the Written Opinion of the International Searching Authority, or the Declaration, dated Mar. 20, 2015, International application No. PCT/US2015/010292, International filing date Jan. 6, 2015.

(Continued)

*Primary Examiner* — Eric D. Bertram

(57) ABSTRACT

An apnea analysis system may include a photoplethysmographic (PPG) sub-system, a breath detection sub-system, and an apnea analysis module. An apnea analysis system includes a photoplethysmographic (PPG) sub-system, a breath detection sub-system, and an apnea analysis module. The PPG sub-system is configured to be operatively connected to an individual and output a PPG signal from the individual. The breath detection sub-system is configured to be operatively connected to the individual and output a breath signal from the individual. The apnea analysis module is in communication with the PPG sub-system and the breath detection sub-system. The apnea analysis module analyzes the breath signal and a respiratory component of the PPG signal and, based on the analysis, identifies a presence of apnea, differentiates between obstructive apnea and central apnea, and provides an indication of the identified apnea.

12 Claims, 12 Drawing Sheets

(51) Int. Cl.
*A61B 5/1455* (2006.01)
*A61B 7/00* (2006.01)
*A61B 5/024* (2006.01)
*A61B 5/08* (2006.01)
*A61B 5/083* (2006.01)
*A61B 5/087* (2006.01)

(52) U.S. Cl.
CPC ........ *A61B 5/0826* (2013.01); *A61B 5/14551* (2013.01); *A61B 5/7278* (2013.01); *A61B 5/7282* (2013.01); *A61B 7/003* (2013.01); *A61B 5/087* (2013.01); *A61B 5/0816* (2013.01); *A61B 5/0836* (2013.01); *A61B 5/1455* (2013.01); *A61B 5/7221* (2013.01); *A61B 5/7225* (2013.01); *A61B 5/7235* (2013.01); *A61B 5/7253* (2013.01); *A61B 5/7264* (2013.01)

(56) References Cited

U.S. PATENT DOCUMENTS

| | | |
|---|---|---|
| 5,285,784 A | 2/1994 | Seeker |
| 5,368,026 A | 11/1994 | Swedlow et al. |
| 5,398,682 A | 3/1995 | Lynn |
| 5,558,096 A | 9/1996 | Palatnik |
| 5,584,295 A | 12/1996 | Muller et al. |
| 5,588,425 A | 12/1996 | Sackner et al. |
| 5,605,151 A | 2/1997 | Lynn |
| 5,862,805 A | 1/1999 | Nitzan |
| 5,865,736 A | 2/1999 | Baker et al. |
| 5,891,023 A | 4/1999 | Lynn |
| 6,002,952 A | 12/1999 | Diab et al. |
| 6,035,223 A | 3/2000 | Baker |
| 6,081,742 A | 6/2000 | Amano et al. |
| 6,095,984 A | 8/2000 | Amano et al. |
| 6,129,675 A | 10/2000 | Jay |
| 6,135,966 A | 10/2000 | Ko |
| 6,178,261 B1 | 1/2001 | Williams et al. |
| 6,223,064 B1 | 4/2001 | Lynn |
| 6,229,856 B1 | 5/2001 | Diab et al. |
| 6,238,351 B1 | 5/2001 | Orr et al. |
| 6,325,761 B1 | 12/2001 | Jay |
| 6,334,065 B1 | 12/2001 | Al-Ali et al. |
| 6,342,039 B1 | 1/2002 | Lynn et al. |
| 6,350,242 B1 | 2/2002 | Doten et al. |
| 6,405,076 B1 | 6/2002 | Taylor et al. |
| 6,463,311 B1 | 10/2002 | Diab |
| 6,506,153 B1 | 1/2003 | Littek et al. |
| 6,561,986 B2 | 5/2003 | Baura et al. |
| 6,564,077 B2 | 5/2003 | Mortara |
| 6,606,511 B1 | 8/2003 | Al-Ali et al. |
| 6,609,016 B1 | 8/2003 | Lynn |
| 6,684,090 B2 | 1/2004 | Al-Ali et al. |
| 6,694,178 B1 | 2/2004 | Soula et al. |
| 6,702,752 B2 | 3/2004 | Dekker |
| 6,709,402 B2 | 3/2004 | Dekker |
| 6,748,252 B2 | 6/2004 | Lynn et al. |
| 6,754,516 B2 | 6/2004 | Mannheimer |
| 6,760,608 B2 | 7/2004 | Lynn |
| 6,783,498 B2 | 8/2004 | Sackner et al. |
| 6,816,741 B2 | 11/2004 | Diab |
| 6,839,581 B1 | 1/2005 | El Solh et al. |
| 6,896,661 B2 | 5/2005 | Dekker |
| 6,905,470 B2 | 6/2005 | Lee et al. |
| 6,925,324 B2 | 8/2005 | Shusterman |
| 6,931,269 B2 | 8/2005 | Terry |
| 6,966,878 B2 | 11/2005 | Schoisswohl et al. |
| 6,970,792 B1 | 11/2005 | Diab |
| 6,980,679 B2 | 12/2005 | Jeung et al. |
| 7,020,507 B2 | 3/2006 | Scharf et al. |
| 7,035,679 B2 | 4/2006 | Addison et al. |
| 7,043,293 B1 | 5/2006 | Baura |
| 7,044,918 B2 | 5/2006 | Diab |
| 7,070,566 B2 | 7/2006 | Medero et al. |
| 7,079,888 B2 | 7/2006 | Oung et al. |
| 7,147,601 B2 | 12/2006 | Marks et al. |
| 7,177,682 B2 | 2/2007 | Lovett |
| 7,190,261 B2 | 3/2007 | Al-Ali |
| 7,215,986 B2 | 5/2007 | Diab et al. |
| 7,218,966 B2 | 5/2007 | Haefner |
| 7,254,425 B2 | 8/2007 | Lowery et al. |
| 7,283,870 B2 | 10/2007 | Kaiser et al. |
| 7,336,982 B2 | 2/2008 | Yoo |
| 7,355,512 B1 | 4/2008 | Al-Ali |
| 7,367,339 B2 | 5/2008 | Bickle |
| 7,367,949 B2 | 5/2008 | Korhonen et al. |
| 7,398,115 B2 | 7/2008 | Lynn |
| 7,403,806 B2 | 7/2008 | Norris |
| 7,407,486 B2 | 8/2008 | Huiku et al. |
| 7,415,297 B2 | 8/2008 | Al-Ali et al. |
| 7,438,683 B2 | 10/2008 | Al-Ali et al. |
| 7,440,787 B2 | 10/2008 | Diab |
| 7,470,235 B2 | 12/2008 | Moriya et al. |
| 7,485,095 B2 | 2/2009 | Shusterman |
| 7,496,393 B2 | 2/2009 | Diab et al. |
| 7,499,835 B2 | 3/2009 | Weber et al. |
| 7,523,011 B2 | 4/2009 | Akiyama et al. |
| 7,561,912 B2 | 7/2009 | Schatz et al. |
| 7,610,324 B2 | 10/2009 | Troyansky et al. |
| 7,690,378 B1 | 4/2010 | Turcott |
| 7,691,067 B2 | 4/2010 | Westbrook et al. |
| 7,706,852 B2 | 4/2010 | Baker |
| 7,801,591 B1 | 9/2010 | Shusterman |
| 7,869,980 B2 | 1/2011 | Casler et al. |
| 7,894,868 B2 | 2/2011 | Al-Ali et al. |
| 7,899,507 B2 | 3/2011 | Al-Ali et al. |
| 7,976,472 B2 | 7/2011 | Kiani |
| 7,988,637 B2 | 8/2011 | Diab |
| 8,019,400 B2 | 9/2011 | Diab et al. |
| 8,046,040 B2 | 10/2011 | Al-Ali et al. |
| 8,130,105 B2 | 3/2012 | Al-Ali et al. |
| 8,203,438 B2 | 6/2012 | Kiani et al. |
| 8,275,553 B2 | 9/2012 | Amundson et al. |
| 8,364,225 B2 | 1/2013 | Diab et al. |
| 8,398,555 B2 | 3/2013 | Ochs et al. |
| 8,515,513 B2 | 8/2013 | Batchelder et al. |
| 8,750,953 B2 | 6/2014 | Ochs et al. |
| 8,758,243 B2 | 6/2014 | Wang et al. |
| 2002/0117173 A1 | 8/2002 | Lynn et al. |
| 2003/0036685 A1 | 2/2003 | Goodman |
| 2003/0158466 A1 | 8/2003 | Lynn |
| 2003/0163054 A1 | 8/2003 | Dekker |
| 2004/0015091 A1 | 1/2004 | Greenwald et al. |
| 2005/0004479 A1 | 1/2005 | Townsend et al. |
| 2005/0022606 A1 | 2/2005 | Partin et al. |
| 2005/0027205 A1 | 2/2005 | Tarassenko et al. |
| 2005/0049470 A1 | 3/2005 | Terry |
| 2005/0070774 A1 | 3/2005 | Addison et al. |
| 2005/0222502 A1 | 10/2005 | Cooper |
| 2005/0222503 A1 | 10/2005 | Dunlop et al. |
| 2006/0122476 A1 | 6/2006 | VanSlyke |
| 2006/0192667 A1 | 8/2006 | Al-Ali |
| 2006/0211930 A1 | 9/2006 | Scharf et al. |
| 2006/0217614 A1 | 9/2006 | Takala et al. |
| 2006/0258921 A1 | 11/2006 | Addison et al. |
| 2007/0004977 A1 | 1/2007 | Norris |
| 2007/0010723 A1 | 1/2007 | Uetela et al. |
| 2007/0073120 A1 | 3/2007 | Li et al. |
| 2007/0073124 A1 | 3/2007 | Li et al. |
| 2007/0129636 A1 | 6/2007 | Friedman et al. |
| 2007/0149890 A1 | 6/2007 | Li et al. |
| 2007/0032639 A1 | 8/2007 | Baker |
| 2007/0213619 A1 | 9/2007 | Linder |
| 2007/0213621 A1 | 9/2007 | Reisfeld et al. |
| 2007/0255146 A1 | 11/2007 | Andrews et al. |
| 2007/0293896 A1 | 12/2007 | Haefner |
| 2008/0066753 A1* | 3/2008 | Martin ............ A61M 16/0051 128/204.23 |
| 2008/0077022 A1 | 3/2008 | Baker |
| 2008/0167540 A1 | 7/2008 | Korhonen et al. |
| 2008/0200775 A1 | 8/2008 | Lynn |
| 2009/0247837 A1 | 10/2009 | Ochs et al. |
| 2009/0326349 A1 | 12/2009 | McGonigle |

(56) References Cited

U.S. PATENT DOCUMENTS

| | | | |
|---|---|---|---|
| 2009/0326395 A1 | 12/2009 | Watson | |
| 2009/0326831 A1 | 12/2009 | McGonigle | |
| 2010/0063366 A1 | 3/2010 | Ochs et al. | |
| 2010/0113904 A1 | 5/2010 | Batchelder et al. | |
| 2010/0113908 A1 | 5/2010 | Vargas et al. | |
| 2010/0113909 A1 | 5/2010 | Batchelder et al. | |
| 2010/0286495 A1 | 11/2010 | McGonigle | |
| 2011/0066062 A1 | 3/2011 | Banet et al. | |
| 2011/0071406 A1 | 3/2011 | Addison et al. | |
| 2011/0190599 A1 | 8/2011 | Wang et al. | |
| 2013/0172759 A1 | 7/2013 | Melker et al. | |
| 2014/0171769 A1* | 6/2014 | Ochs .................. | A61B 5/4818 600/324 |
| 2014/0275887 A1 | 9/2014 | Batchelder et al. | |
| 2014/0275938 A1 | 9/2014 | Addison et al. | |

FOREIGN PATENT DOCUMENTS

| | | |
|---|---|---|
| EP | 1507474 B1 | 2/2009 |
| WO | 00/21438 A1 | 4/2000 |
| WO | 03/000125 A1 | 1/2003 |
| WO | 03/055395 A1 | 7/2003 |
| WO | 03/084396 A1 | 10/2003 |
| WO | 2004/075746 A2 | 9/2004 |
| WO | 2010/030238 A1 | 3/2010 |

OTHER PUBLICATIONS

PCT Notification of Transmittal of the International Search Report and the Written Opinion of the International Searching Authority, or the Declaration (PCT Rule 441), dated Apr. 3, 2014, Covidien LP et al., International Filing Date Dec. 18, 2013.

International Search Report and Written Opinion of the International Searching Authority for application No. PCT/US2013/075944, dated Apr. 3, 2014.

Lindberg, L.G., Ughall, H., Oberg, P.A., "Monitoring of respiratory and heart rates using a fibre-optic sensor," Medical & Biological Engineering & Computing, Sep. 1992, pp. 533-537.

Rapaport and Cousin, "New phase-lock tracking instrument for foetal breathing monitoring," Med. & Bioi. Eng. & Camp. 1982, vol. 20, pp. 1-6.

Risk, Lofsky, Ann MD, Sleep Apnea and Narcotic Postoperative Pain Medication: A Morbidity and Mortality; http://www.apsf.org/newsletters/html/2002/summer/04sleepapnea.htm.

Stagg and Gennser, "Electronic analysis of foetal breathing movements: A practical application of phase-locked-loop principles," Journal of Med. Eng. and Tech., Sep. 1978, vol. 2, No. 5, pp. 246-249.

Thomas, R. J, Mietus, J. E., Peng, Chung-Kang; Gilmartin, Geoffrey, Daly, R>W., Goldberger, A. L., Gottlieb, D.J., "Differentiating Obstructive from Central and Complex Sleep Apnea Using an Automated Electrocardiogram-Based Method", Sleep, vol. 30, No. 12, 2007.

Waugh et al, Comparison of Apnea Detection by Pulse Oximetry Versus Capnography, AARC Congress, Orlando FL, Poster, 2007.

* cited by examiner

FIG. 10

| CO2 Waveform | SPO2 | Respiration | Respiration Effort | Condition/Alarm |
|---|---|---|---|---|
| Breaths Present | >85% | Present | Normal | Regular Respiration |
| Breaths Absent | >85% | None | None | Initial Stages of Central Apnea - may become long term central event or morph into a mixed apnea. Alarm after set time exceeded |
| Breaths Absent | <85% or dropping rapidly | None | None | Longer Term or More Severe Central Apnea - High Alarm. |
| Breaths Absent | >85% | Present | High | Possible Obstructive Apnea. Alarm after set time. |
| Breaths Absent | >85% | Present | Normal | Possible Disconnected Probe. Alarm as such. |
| Breaths Intermittent/Cycling | <85% or fluctuating markedly | Intermittent/Cycling | Intermittent/Cycling | Apnea Events (perhaps mixed) over longer time scales may be mark/score severity for later clinical use rather than alarm |

APNEA ANALYSIS SYSTEM AND METHOD

FIELD

Embodiments of the present disclosure generally relate to physiological signal processing and, more particularly, to an apnea analysis system and method, such as may be used to detect and classify types of apnea.

BACKGROUND

Capnography represents a system and method of monitoring and displaying carbon dioxide ($CO_2$) level(s), $CO_2$ waveform(s), and/or other $CO_2$ related parameters, such as End Tidal $CO_2$ ($EtCO_2$), or a concentration or partial pressure of $CO_2$, from an entire inhalation and exhalation respiratory cycle of an individual. A typical capnographic system generates waveforms and numeric values of an individual's respiratory cycle, and may be used to identify adverse ventilation events.

Apnea may be detected using a capnographic system. For example, if a capnograph indicates that no exhaled $CO_2$ is present, then apnea may be present. However, a typical capnographic system is unable to differentiate between types of apnea. Instead, a typical capnographic system is generally only able to indicate that apnea exists. Because the specific type of apnea may not be readily determined through analysis of a capnographic signal or waveform, proper diagnosis and treatment may be hindered.

SUMMARY

Embodiments of the present disclosure generally relate to physiological signal processing and, more particularly, to an apnea analysis system and method, such as may be used to detect and classify types of apnea. In an embodiment, a monitoring system receives a photoplethysmographic (PPG) signal from a PPG sensor, and a breath signal from a breath sensor, and analyzes the two signals to determine if the patient is breathing normally. The system analyzes the PPG signal to determine whether the patient is breathing or attempting to breathe. This analysis is based on the identification of a respiratory component of the PPG signal, as discussed below. The system also analyzes the breath signal to determine if the patient is actually breathing. The system then compares these two signals to determine if the patient is experiencing apnea, and to differentiate between obstructive apnea and central apnea. In various embodiments, the system also identifies probe-off conditions for both the PPG sensor and the breath sensor, based on the comparison of the two signals.

In an embodiment, an apnea analysis system includes a photoplethysmographic (PPG) sub-system, a breath detection sub-system, and an apnea analysis module. The PPG sub-system is configured to be operatively connected to an individual and output a PPG signal from the individual. The breath detection sub-system is configured to be operatively connected to the individual and output a breath signal from the individual. The apnea analysis module is in communication with the PPG sub-system and the breath detection sub-system. The apnea analysis module analyzes the breath signal and a respiratory component of the PPG signal and, based on the analysis, identifies a presence of apnea, differentiates between obstructive apnea and central apnea, and provides an indication of the identified apnea.

In an embodiment, an apnea analysis method includes receiving a photoplethysmographic (PPG) signal indicative of a cardiac status of an individual, and receiving a breath signal indicative of a breathing status of the individual. The method identifies a respiratory component of the PPG signal indicative of a respiration effort or a respiration rate, and compares the breath signal and the respiratory component of the PPG. The method also includes identifying a presence of apnea, and differentiating between obstructive apnea and central apnea, based on the comparison.

In an embodiment, a tangible and non-transitory computer readable medium includes one or more sets of instructions configured to direct a computer to analyze a respiratory component of a PPG signal and a breath signal to detect whether or not an individual is experiencing apnea. The instructions also include differentiating between obstructive apnea and central apnea based on the analysis of the respiratory component of the PPG signal and the breath signal.

In an embodiment, a system for classifying an apnea includes a PPG sub-system, a breath detection sub-system, and an apnea analysis module. The PPG sub-system is configured to output a first signal indicative of a respiratory component of a PPG signal from a patient over a time period. The breath detection sub-system is configured to output a second signal indicative of a presence of breaths from the patient over the time period. The apnea analysis module is configured to identify and classify an apnea based on the first and second signals.

In an embodiment, a system for classifying an apnea includes at least one processor configured to receive a breath signal and a respiratory rate or effort signal, identify a reduction in one of the breath signal or the respiratory rate or effort signal over a time period, identify a corresponding status of the other of the breath signal or the respiratory rate or effort signal over at least a portion of the time period, and classify a type of apnea based on the reduction in the one of the breath signal or the respiratory rate or effort signal and the corresponding status of the other of the breath signal or the respiratory rate or effort signal.

Certain embodiments of the present disclosure provide a tangible and non-transitory computer readable medium that includes one or more sets of instructions configured to direct a computer to analyze a PPG signal received from a PPG sub-system and a breath signal received from a breath detection sub-system to detect whether or not an individual is experiencing apnea, and differentiate between obstructive apnea, central apnea, and a combination of obstructive apnea and central apnea based on the analysis of the PPG signal and the breath signal.

BRIEF DESCRIPTION OF THE DRAWINGS

FIG. 10 illustrates a logic table that may be used with an apnea analysis system and method, according to an embodiment of the present disclosure.

DETAILED DESCRIPTION

Figure 1:
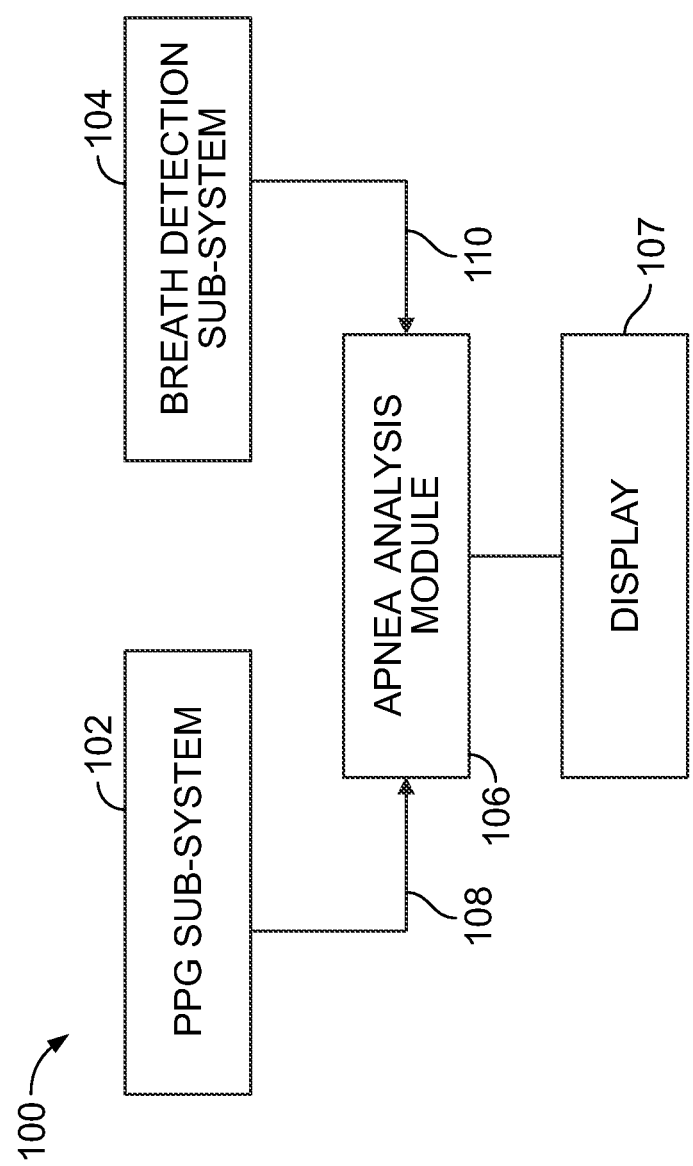
FIG. 1 illustrates a simplified block diagram of an apnea analysis system, according to an embodiment of the present disclosure.

Embodiments of the present disclosure generally relate to physiological signal processing and, more particularly, to an apnea analysis system and method, such as may be used to detect and classify types of apnea. In an embodiment, a monitoring system receives a photoplethysmographic (PPG) signal from a PPG sensor, and a breath signal from a breath sensor, and analyzes the two signals to determine if the patient is breathing normally. The system analyzes the PPG signal to determine whether the patient is breathing or attempting to breathe. This analysis is based on the identification of a respiratory component of the PPG signal, as discussed below. The system also analyzes the breath signal to determine if the patient is actually breathing. The system then compares these two signals to determine if the patient is experiencing apnea, and to differentiate between obstructive apnea and central apnea. In various embodiments, the system also identifies probe-off conditions for both the PPG sensor and the breath sensor, based on the comparison of the two signals.

Apnea is the cessation or significant decrease in respiration or airflow by an individual. Obstructive apnea (or obstructive sleep apnea) is apnea in the presence of respiratory effort. That is, obstructive apnea is generally indicated by the existence of an effort to breathe, but with decreased or no actual breath exhalation. For example, an individual may try to breathe, as evident by chest movement, but the individual produces no actual breath. Such a situation may exist when the individual's airway is constricted or blocked.

Central apnea, or central sleep apnea, is apnea without respiratory effort. During central apnea, an individual may stop breathing, and may exhibit no effort or drive to breathe. Unlike obstructive apnea, with central apnea there is generally no chest movement or struggling. Central apnea may be characterized by an imbalance of respiratory control centers within the brain. Blood and carbon dioxide levels, and the neurological feedback mechanism that monitors them, may not react quickly enough to maintain an even respiratory rate. The basic neurological controls for breathing malfunction and fail to provide the signal to inhale, causing the individual to miss one or more cycles of breathing. If the pause in breathing is long enough, the percentage of oxygen in the individual's circulation may drop to a lower than normal level (hypoxaemia) and the concentration of carbon dioxide may build to a higher than normal level (hypercapnia). In turn, the conditions of hypoxaemia and hypercapnia may trigger additional adverse effects on the body, such as brain damage and even death.

Further, some individuals suffer from a combination of obstructive and central apnea, namely a mixed apnea. When obstructive apnea is severe and longstanding, episodes of central apnea sometimes develop.

Accordingly, in clinical situations, it can be helpful to monitor a patient's breathing status, identify episodes of apnea, and categorize such episodes as central or obstructive apnea, in order to alert caregivers and enable them to provide the necessary attention and response to the patient.

An apnea analysis system is provided for monitoring a breathing status of a patient in order to identify and classify episodes of apnea. An apnea analysis system 100 according to an embodiment is shown in FIG. 1. In the embodiment shown, the apnea analysis system 100 includes a photoplethysmographic (PPG) sub-system 102 and a breath detection sub-system 104 operatively connected to and in communication with an apnea analysis module 106, which may be operatively connected to a display 107. The PPG sub-system 102 is configured to be operatively connected to an individual and used to output a PPG signal or output 108 indicative of one or more physiological characteristics of the individual. For example, the PPG signal may be indicative of a blood flow status or cardiac status of the patient, and may be obtained through a pulse oximeter. The PPG sub-system 102 may include a PPG sensor (such as a pulse oximetry sensor) that is positioned on a finger, forehead, forearm, or the like of the individual. As described below, the PPG sensor is configured to detect the PPG signal or output 108, which may be in the form of a PPG signal or a respiratory component of the PPG signal. The PPG signal 108 may be analyzed to determine physiological characteristics such as respiration rate, respiratory effort, pulse rate, oxygen saturation, and/or other parameters.

The breath detection sub-system 104 is configured to be operatively connected to the individual and output a breath signal indicative of a breathing status of the individual, such as by detecting exhaled breath of an individual. For example, the breath detection sub-system 104 may include a sampling device, such as nasal prongs, a breathing mask, and/or the like, configured to be positioned on the individual. The sampling device may be connected to a sidestream or mainstream gas analyzer. In at least one embodiment, the breath detection sub-system 104 is a capnographic sub-system. Alternatively, the breath detection sub-system 104 may be or include pressure, acoustic, moisture, and/or temperature-based breath analysis sub-systems that are configured to detect the presence of inhaled and/or exhaled breath. The breath detection sub-system 104 is configured to output a breath signal or output 110 indicative of a breathing status of the individual. The breath signal or output 110 may indicate whether the individual is inhaling and/or exhaling, and may indicate characteristics of the individual's breath, such as depth, duration, $CO_2$ content, and frequency.

The PPG sub-system 102 and the breath detection sub-system 104 may be connected to the apnea analysis module 106 through wired or wireless connections. As shown in FIG. 1, the apnea analysis module 106 receives the PPG signal or output 108 from the PPG sub-system 102, as well as the breath signal or output 110 from the breath detection sub-system 104. The apnea analysis module 106 analyzes the outputs 108 and 110 from the PPG sub-system 102 and the breath detection sub-system 104, respectively, and detects whether the individual is experiencing apnea. Moreover, based on the analysis of the outputs 108 and 110, the apnea analysis module 106 is able to classify the apnea as central, obstructive, or mixed apnea, as described in further detail below.

Figure 2:
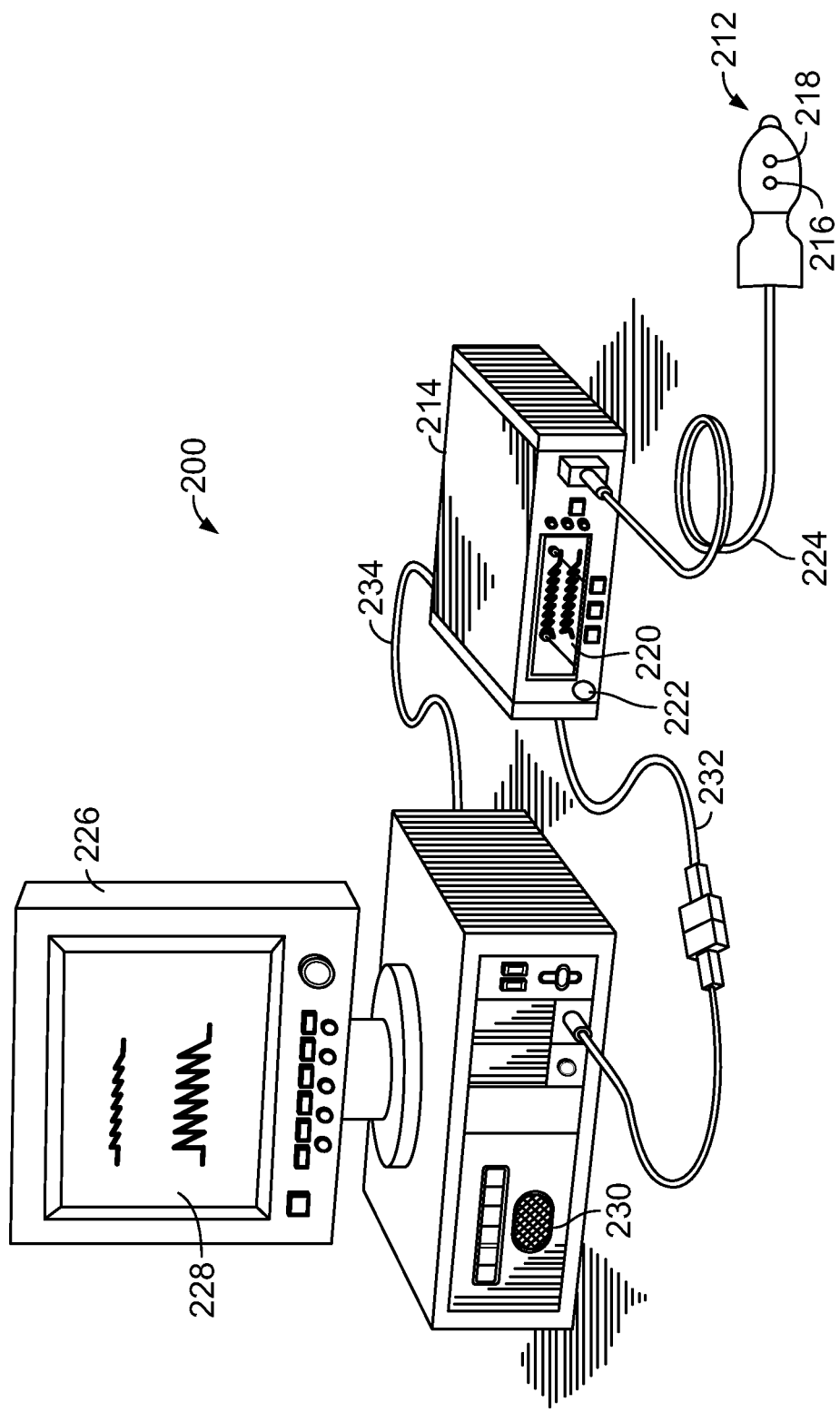
FIG. 2 illustrates an isometric view of a PPG system, according to an embodiment of the present disclosure.

A PPG system 200 according to an embodiment is shown in FIG. 2. The PPG system 200 represents an example of the PPG sub-system 102 shown in FIG. 1. In an embodiment, the PPG system 200 is a pulse oximetry system. A pulse oximeter detects changes in blood volume under the skin, and thereby can indirectly, non-invasively measure the oxygen saturation of hemoglobin in an individual's arterial blood (as opposed to measuring oxygen saturation directly by analyzing a blood sample taken from the patient). Pulse oximeters may also be used to measure the pulse rate of the patient.

The pulse oximetry system 200 includes a sensor or probe 212 that is placed at a site on a patient, typically a fingertip, toe, forehead or earlobe, or in the case of a neonate, across a foot. The sensor includes a light source or emitter 216 and a photodetector 218. Light passes from the emitter 216 through the patient's blood perfused tissue and to the detector 218, which photoelectrically senses the absorption of the light in the tissue. For example, the oximeter may measure the intensity of light that is attenuated by the tissue and received at the detector, as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The PPG signal may be analyzed to identify cardiac pulses and determine the patient's pulse rate and when each cardiac pulse occurs.

When two or more wavelengths of light are emitted, the relative light intensity or the amount of light absorbed by each may be used to calculate the amount of a particular component in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less red light and more infrared light than blood with a lower oxygen saturation. By comparing the intensities of light at the two wavelengths at different points in the pulse cycle, it is possible to estimate the blood oxygen saturation of hemoglobin in arterial blood.

Referring again to FIG. 2, the emitter 216 may emit two or more wavelengths into the patient's tissue, in order to calculate oxygen saturation of the patient's blood. Although only one emitter 216 is shown, the PPG sub-system 200 may include a plurality of emitters and detectors, and/or a plurality of sensors 212 forming a sensor array instead of a single sensor.

The PPG sub-system 200 also includes a monitor 214. The sensor 212 may be connected to and draw power from the monitor 214, as shown. Alternatively, the sensor 212 may be wirelessly connected to the monitor 214 and include its own battery or similar power supply. The monitor 214 may be configured to calculate physiological parameters based at least in part on data received from the sensor 212 relating to light emission and detection. Alternatively, the calculations may be performed on the sensor 212 or in the sensor cable 224, and the result of the oximetry reading may be passed to the monitor 214. Further, the monitor 214 may include a display 220 configured to display the physiological parameters or other information about the PPG sub-system 200. As shown, the monitor 214 may also include a speaker 222 to provide an audible sound that may be used in various other embodiments, such as for example, sounding an audible alarm in the event that a patient's physiological parameters are not within a predefined normal range.

The sensor 212, or the sensor array, may be communicatively coupled to the monitor 214 via the cable 224. In other embodiments, a wireless transceiver (not shown) or the like may be used instead of or in addition to cable 224 to transmit data between the sensor and monitor.

The PPG sub-system 200 may also include a multi-parameter patient monitor 226. The monitor 226 may be a cathode ray tube type, a flat panel display (as shown) such as a liquid crystal display (LCD) or a plasma display, or any other type of monitor now known or later developed. The monitor 214 may be communicatively coupled to the multi-parameter patient monitor 226 via a cable 232 or 234. The multi-parameter patient monitor 226 may be configured to calculate physiological parameters and to provide a display 228 for information from the monitor 214 and from other medical monitoring devices or systems, such as, for example, the apnea analysis module 106 shown in FIG. 1. For example, the multiparameter patient monitor 226 may be configured to display an estimate of an individual's blood oxygen saturation (referred to as an "$SpO_2$" measurement) generated by the monitor 214, pulse rate information from the monitor 214 and blood pressure from a blood pressure monitor (not shown) on the display 228. The monitor 226 may be used as the display 107 of FIG. 1.

Figure 3:
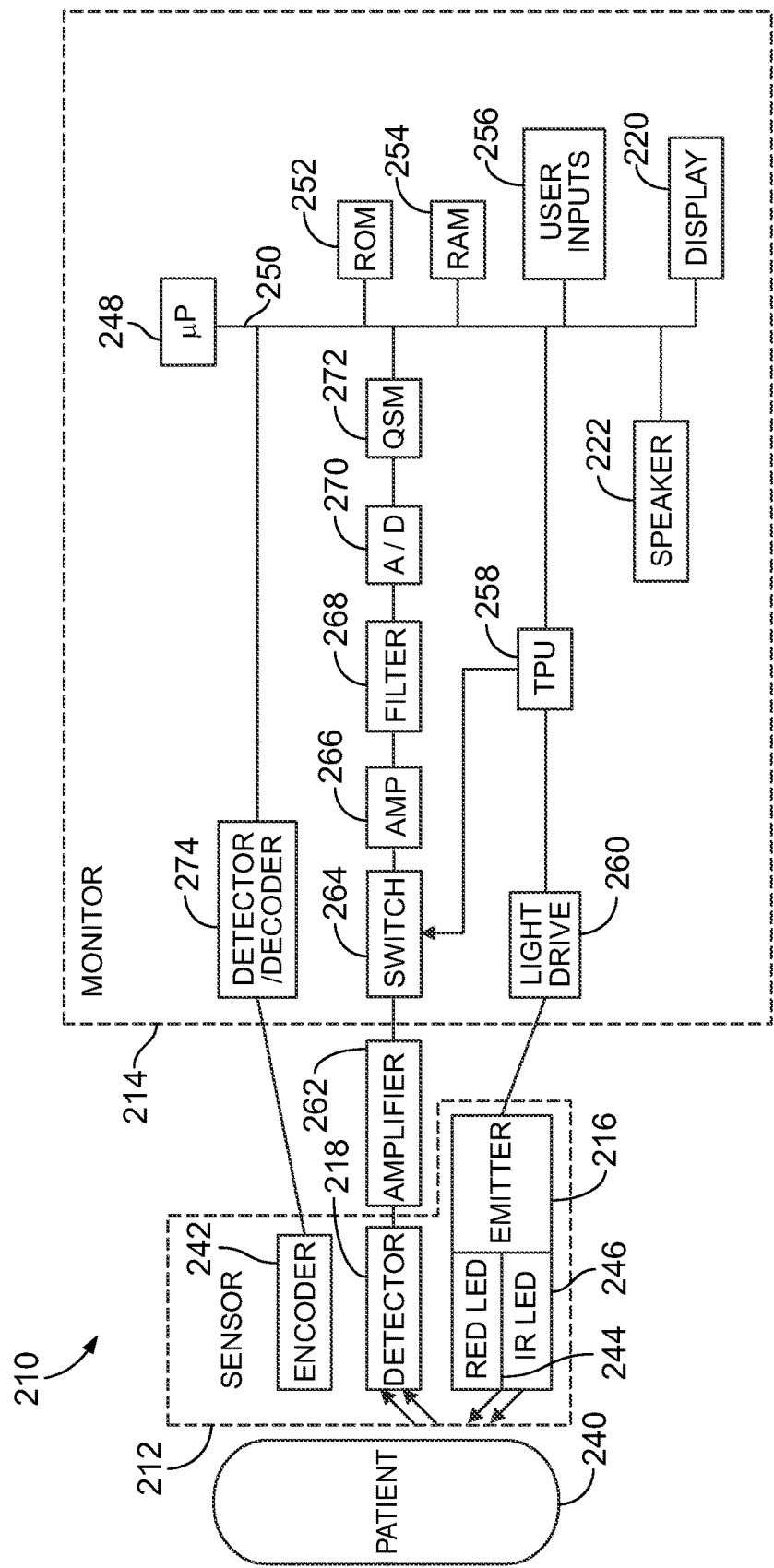
FIG. 3 illustrates a simplified block diagram of a PPG system, according to an embodiment of the present disclosure.

A block diagram of a PPG system 210 according to an embodiment is shown in FIG. 3. Certain illustrative components of the sensor 212 and the monitor 214 are illustrated in FIG. 3. The sensor 212 includes the emitter 216, the detector 218, and an encoder 242. The emitter 216 includes a first light emitting light source for emitting light at a first wavelength, such as RED light emitting diode (LED) 244, and a second light emitting light source for emitting light at a second wavelength, such as IR LED 246. The emitter 216 emits light into the patient's tissue 240 at the wavelengths used to calculate the patient's physiological parameters, such as $SpO_2$. In at least one embodiment, the RED wavelength is between about 600 nm and about 700 nm, and the IR wavelength is between about 800 nm and about 1000 nm. In embodiments where a sensor array is used in place of single sensor, each sensor may be configured to emit a single wavelength. For example, a first sensor emits only a RED light while a second only emits an IR light. In various embodiments, more than two wavelengths may be emitted by one or more emitters.

In at least one embodiment, the detector 218 is configured to detect the intensity of light at the two emitted wavelengths. In operation, light may enter the detector 218 after passing through the patient's tissue 240. The detector 218 converts the intensity of the received light into an electrical signal. The light intensity is directly related to the absorbance and/or reflectance of light in the tissue 240. That is, when more light at a certain wavelength is absorbed or reflected, less light of that wavelength is received from the tissue by the detector 218. After converting the received light to an electrical signal, the detector 218 sends the signal to monitor 214, where the microprocessor 248 may use algorithms and/or look-up tables to calculate physiological parameters (such as $SpO_2$, respiration rate, respiratory effort, and pulse rate), based on the time-varying absorption of the light in the patient's tissue 240.

The encoder 242 may contain information about the sensor 212, such as the type of sensor (for example, whether the sensor 212 is intended for placement on a forehead or digit) and the wavelengths of light emitted by the emitter 216. The information may be used by the monitor 214 to select appropriate algorithms, lookup tables and/or calibration coefficients stored in the monitor 214 for calculating the patient's physiological parameters. The encoder 242 may contain information specific to the patient 240, such as, for example, the patient's age, weight, and diagnosis. The encoder 242 may, for instance, be a coded resistor which stores values corresponding to the type of sensor 212, and/or the wavelengths of light emitted by the emitter 216, or the encoder 242 may include a memory on which such information is stored. User inputs 256 and display 220 may be used to enter information about the patient, such as age, weight, height, diagnosis, medications, treatments, and so forth.

Signals from the detector 218 and the encoder 242 are transmitted to the monitor 214, through a decoder 274. The monitor 214 may include a general-purpose microprocessor 248 connected to an internal bus 250. The microprocessor 248 may be adapted to execute software, which may include an operating system and one or more applications, as part of performing the functions described herein. Also connected to the bus 250 may be a read-only memory (ROM) 252, a random access memory (RAM) 254, user inputs 256, display 220, and speaker 222. Any suitable computer-readable media may be used in the system for data storage.

As shown, a time processing unit (TPU) 258 may provide timing control signals to a light drive circuitry 260, which controls when the emitter 216 is illuminated and multiplexed timing for the two LED's 244 and 246. The TPU 258 may also control the gating-in of signals from detector 218 through an amplifier 262 and a switching circuit 264. The signals are sampled at the proper time, depending upon which light source is illuminated. The received signal from the detector 218 may be passed through an amplifier 266, a low pass filter 268, and an analog-to-digital converter 270. The digital data may then be stored in a queued serial module (QSM) 272 (or buffer) for later downloading to RAM 254 as QSM 272 fills up.

Figure 4A:
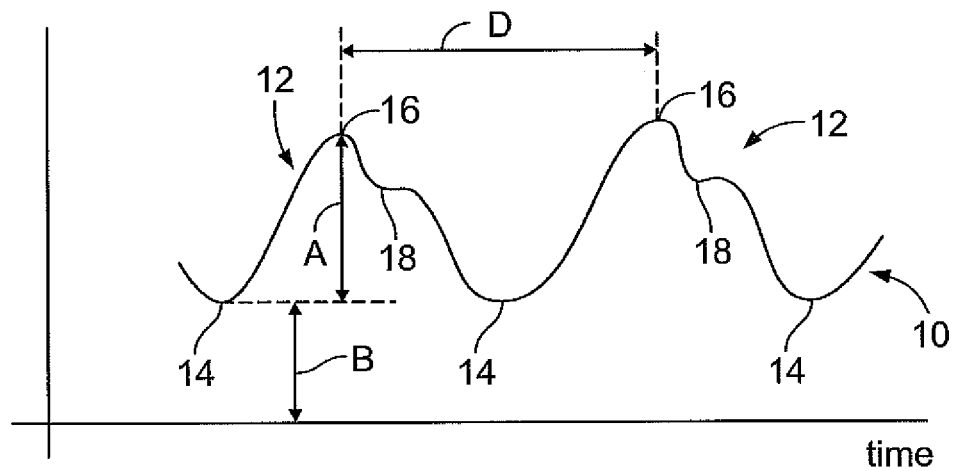
FIG. 4A illustrates a portion of a PPG waveform, according to an embodiment of the present disclosure.

An example of a PPG signal obtained from a pulse oximeter (such as PPG system 102, 200, 210) is shown in FIG. 4A. The PPG signal may be output as a PPG waveform 10 which represents the absorption of light by the patient's tissue over time. The PPG waveform 10 includes cardiac pulses 12, where absorption of light increases due to the increased volume of blood in the arterial blood vessel due to the cardiac pulse. Each cardiac pulse 12 may be identified based on a valley 14, peak 16, dichrotic notch 18, and subsequent valley 14. The cardiac pulse 12 includes an amplitude A measured at any suitable location along the pulse, such as along the upstroke of the pulse, from the preceding valley 14 to the peak 16. The PPG waveform 10 includes a pulse period of duration D between adjacent pulses 12. The duration D is shown measured from one peak 16 to an adjacent peak 16, but may be measured between any suitable points along the pulses. The PPG waveform 10 also includes a baseline shift B indicating a baseline level of the light absorption, above which the waveform modulates due to arterial blood pulses. The baseline B may also be measured at any suitable point along the waveform 10, such as at the valleys 14, peaks 16, or a median or mean value between the peaks and valleys. The PPG waveform 10 shown in FIG. 4A may be the output 108 of FIG. 1.

Figure 4B:
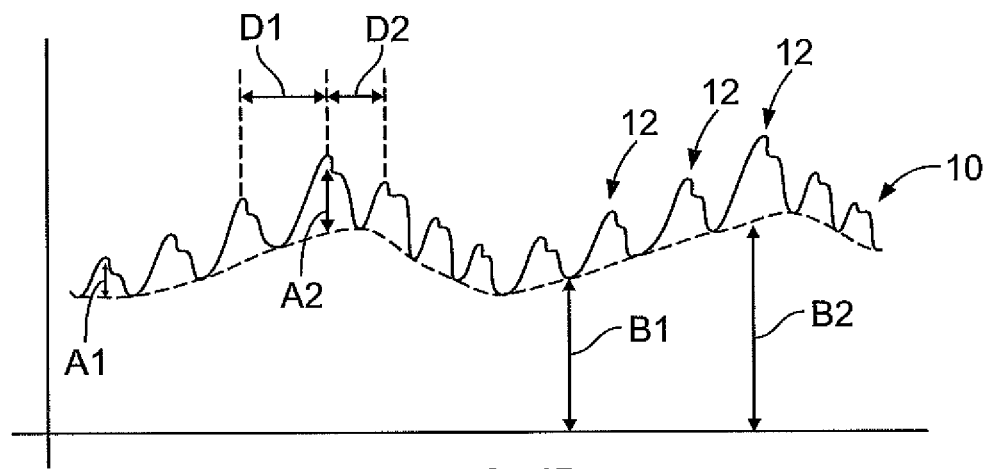
FIG. 4B illustrates a PPG waveform during normal breathing, according to an embodiment of the present disclosure.

A segment of a PPG waveform 10 during normal breathing, or attempts to breathe, is shown in FIG. 4B. The waveform 10 includes cardiac pulses 12. It should be noted that the number of cardiac pulses 12 per breath is not necessarily to scale, and may vary from patient to patient. Respiration or attempted respiration (breathing in and out, or attempting to breathe) may cause one or more of three modulations in the PPG waveform 10.

The first modulation is a modulation of the baseline B of the PPG waveform 10. The effect of the patient breathing in and out causes the baseline B of the waveform 10 to move up and down, cyclically, with the patient's respiration rate. The baseline shift is due in part to the shifting of venous blood at the peripheries during the respiratory cycle. As the patient inhales, the lowering of the thoracic pressure causes an increase in the driving pressure gradient from the peripheries to the heart. Relatively more blood is drained from the peripheries causing less light to be absorbed. During exhalation, the thoracic pressure increases, the pressure gradient reduces, and more blood begins to pool at the peripheries, causing more light to be absorbed. This process is repeated with each breath. The baseline modulation waveform B may be tracked by following any component of the PPG waveform 10, such as the peaks, valleys, dichrotic notches, median value, or other value. As shown in FIG. 4B, the baseline B1 at one point in time is smaller than the baseline B2 at a later time.

The second respiration-induced modulation of the PPG is a modulation of the amplitude A. As the patient breathes in and out, the amplitude A of each cardiac pulse 12 increases and decreases, with larger amplitudes (such as amplitude A2) tending to coincide with the top of the baseline shift B, and smaller amplitudes (such as amplitude A1) tending to coincide with the bottom of the baseline shift.

The third modulation due to respiration is a modulation of the frequency or duration of the cardiac pulses 12. This modulation may also be characterized in terms of the duration between pulses. On the upstroke of the baseline of the waveform 10, which tends to coincide with inhalation, the frequency tends to decrease, with a longer duration D (such as duration D1 in FIG. 4B) between cardiac pulses 12. On the downstroke of the baseline of the waveform 10, which tends to coincide with exhalation, the frequency tends to increase, with a shorter duration (such as duration D2) between the cardiac pulses 12.

Figure 4C:
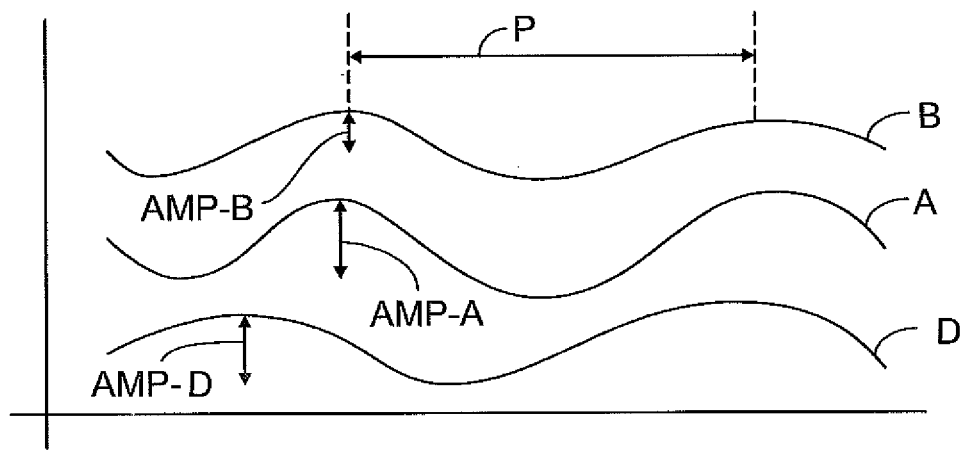
FIG. 4C illustrates one or more respiratory components of the PPG during normal breathing, according to an embodiment of the present disclosure.

Each of these three modulations—modulations of baseline B, cardiac pulse amplitude A, and duration D between cardiac pulses (or frequency of pulses)—may be referred to as a respiratory component of the PPG signal, or a respiratory-induced modulation of the PPG signal. These three modulations are plotted in FIG. 4C, which shows the frequency modulation waveform D, the amplitude modulation waveform A, and the baseline modulation waveform B.

These waveforms indicate the cyclical increase and decrease in these values (frequency, amplitude, and baseline) due to the patient's respiration. It should be noted that in any particular patient, one, two, or all three of these modulations may be present. That is, a particular individual may exhibit only the baseline modulation, or only the amplitude modulation, or only the frequency modulation of the PPG, or a combination of two, or all three of these modulations. As referred to herein, a respiratory component of the PPG includes any one of these respiratory-induced modulations of the PPG waveform 10, or a combination of them.

The apnea analysis module 106 and/or the PPG sub-system 102 may monitor the PPG waveform 10 for variations or modulations in one or more of the baseline modulation waveform B, the cardiac pulse amplitude modulation waveform A, and the cardiac pulse frequency waveform F (or duration D) to determine whether or not an individual is breathing properly. Additionally, the apnea analysis module 106 and/or the PPG sub-system 102 may monitor two or more of the above to determine a confidence level in the analysis. For example, if two or more of the respiratory components correlate with respect to the existence and rate of the variation or modulation (that is, the rate of modulation of the two or more components matches or closely matches), then a high degree of confidence in the analysis exists. If one of the respiratory components does not correlate with the other one or two components, then a moderate to low degree of confidence in the analysis exists. The apnea analysis module may assess the degree of correlation or matching between the respiratory components in order to assess a degree of confidence, with a higher correlation indicating a higher confidence, and vice versa. The apnea analysis module 106 and/or the PPG sub-system 102 may output a confidence metric (such as high, moderate, or low) based on the agreement or lack of agreement between the three respiratory components.

The respiratory component(s) of the PPG may be used to identify the patient's respiration rate (also known as pulmonary ventilation rate, respiratory rate, ventilation rate, or breathing frequency). For example, referring to FIG. 4C, the period P of one or more of the waveforms A, B, and D may signify the patient's respiration rate. Further, the amplitude of one or more of the waveforms A, B, and D may indicate a respiratory effort of the patient—that is, the effort exerted by the patient to breathe. For example, an increase in the amplitude of one or more waveforms A, B, and D (marked "AMP-A", "AMP-B", and "AMP-D", respectively) from a relative baseline may indicate that the patient has increased his or her effort to breathe, and a decrease in amplitude may indicate a decrease in the patient's effort to breathe. The amplitude(s) of the waveform(s) A, B, and/or D may be used to track a trend in the patient's respiratory effort. An increase in the respiratory rate may also indicate an increased respiratory effort by the patient. In an embodiment, the PPG sub-system 102 and/or the apnea analysis module 106 outputs a respiratory rate signal and/or a respiratory effort signal that tracks these parameters over time.

The PPG sub-system 102 may detect and determine the respiration rate of an individual, as described in United States Patent Application Publication No. 2011/0071406, entitled "Determining a Characteristic Respiration Rate," which is hereby incorporated by reference in its entirety. The PPG sub-system 102 may be used to detect and determine the respiration rate and/or the respiratory effort of an individual, as described in U.S. application Ser. No. 13/867,291, entitled "System and Method for Determining Respiratory Parameters From Blood Flow Signals," which is also hereby incorporated by reference in its entirety.

The output 108 from the PPG sub-system 102 may include one or more of the PPG waveform 10, the respiratory component waveforms A, B, and D, a respiratory rate signal, a respiratory effort signal, and combinations of these. The PPG waveform 10 may be a raw signal from the PPG sensor indicating light absorbance over time, or may be a filtered and processed waveform with filtering steps such as noise reduction, artifact removal, etc. The PPG sub-system 102, such as the PPG sub-system 200, provides the PPG signal or output 108 to the apnea analysis module 106.

Figure 5A:
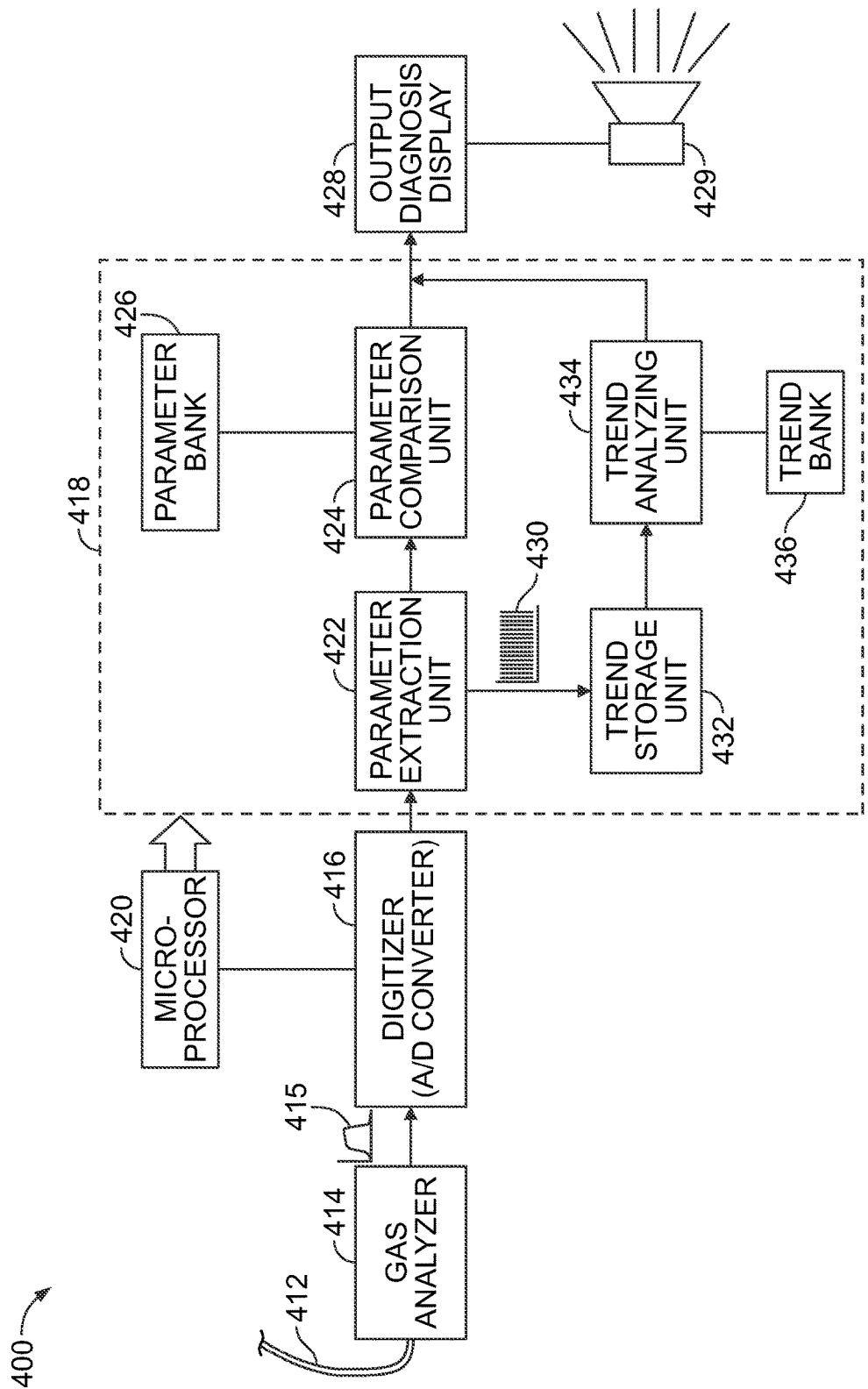
FIG. 5A illustrates a schematic block diagram of a capnographic sub-system, according to an embodiment of the present disclosure.

Turning now to the breath-detection sub-system, a schematic block diagram of a capnographic sub-system 400, according to an embodiment of the present disclosure, is shown in FIG. 5A. The capnographic sub-system 400 is an example of a breath detection sub-system 104, as shown in FIG. 1. The capnographic sub-system 400 is used to detect respiration of an individual and provide a breath output, such as the breath output 110 (shown in FIG. 1) to the apnea analysis module 106. The breath detection sub-system includes a breath-sampling interface (such as nasal prongs, a gas sampling mask, or the like) configured to be connected to the individual. The signal or output 110 of the breath detection sub-system 104 may be a breath waveform, such as a capnographic waveform, as described below.

Alternatively, various other breath detection sub-systems other than capnographic sub-systems may be used. For example, the output 110 may be a pressure signal, moisture signal, temperature signal, acoustic signal, or the like, detected and sent from a corresponding breath detection sub-system 104 that is operatively connected to an individual. For example, a pressure transducer may be positioned proximate to a mouth or airway of the individual and, through cyclical changes in airflow pressure, may indicate exhaled breath. Similarly, a temperature or moisture sensor may indicate exhaled breath through cyclical temperature or moisture changes of exhaled airflow. Further, an acoustic sensor, such as a microphone, proximate to a mouth or an airway may detect exhaled breath through cyclical changes in acoustic signals within the mouth or airway.

An embodiment of a capnographic sub-system 400 is shown in FIG. 5A. Samples of the breath of a patient are drawn through a sampling tube 412 into a gas analyzer 414. The gas analyzer 414 analyzes the patient's breath for $CO_2$ content, and an electronic output signal is generated, such as waveform 415, corresponding to the instantaneous concentration levels of $CO_2$ in the individual's breath. The analog $CO_2$ waveform signals 415 generated by the gas analyzer 414 may be input into a digitizer 416, such as an A/D converter, where the analog signals are converted into a serial digital train of data for processing.

Analysis of the waveform data is performed in a signal processing unit 418. The signal processing unit 418 may be controlled by a general-purpose microprocessor 420. The digital waveform signals may be input into a parameter extraction unit 422, where the shape of each waveform is analyzed, and morphology parameters of the waveform are extracted. The parameters extracted in the parameter extraction unit 422 may be stored as a matrix, which is input into a parameter comparison unit 424. The parameter comparison unit 424 compares the matrix to a reference matrix from a reference set stored in the parameter bank 426. The reference matrix includes parameters of a typical breath waveform obtained from a normal subject.

In addition to outputting a matrix of all of the extracted waveform parameters of a single waveform, the waveform parameter extraction unit 422 may also output a continuous data stream corresponding to the parameters obtained from a sequence of breath waveforms. The serial values of the parameters may be input into a trend storage unit 432, and on demand, into a trend analyzing unit 434 where any long term trend is detected in the value of any of the parameters selected. Any long term trend is compared in the trend analyzing unit 434 with reference trends stored in the trend bank 436. The establishment of any abnormality in the observed trend may result in the output of an informative message to the operator on the output diagnosis display device 428. The capnographic sub-system 400 may be programmed to actuate an audible or visible alarm 429 based on recognized emergency or alert conditions.

Figure 5B:
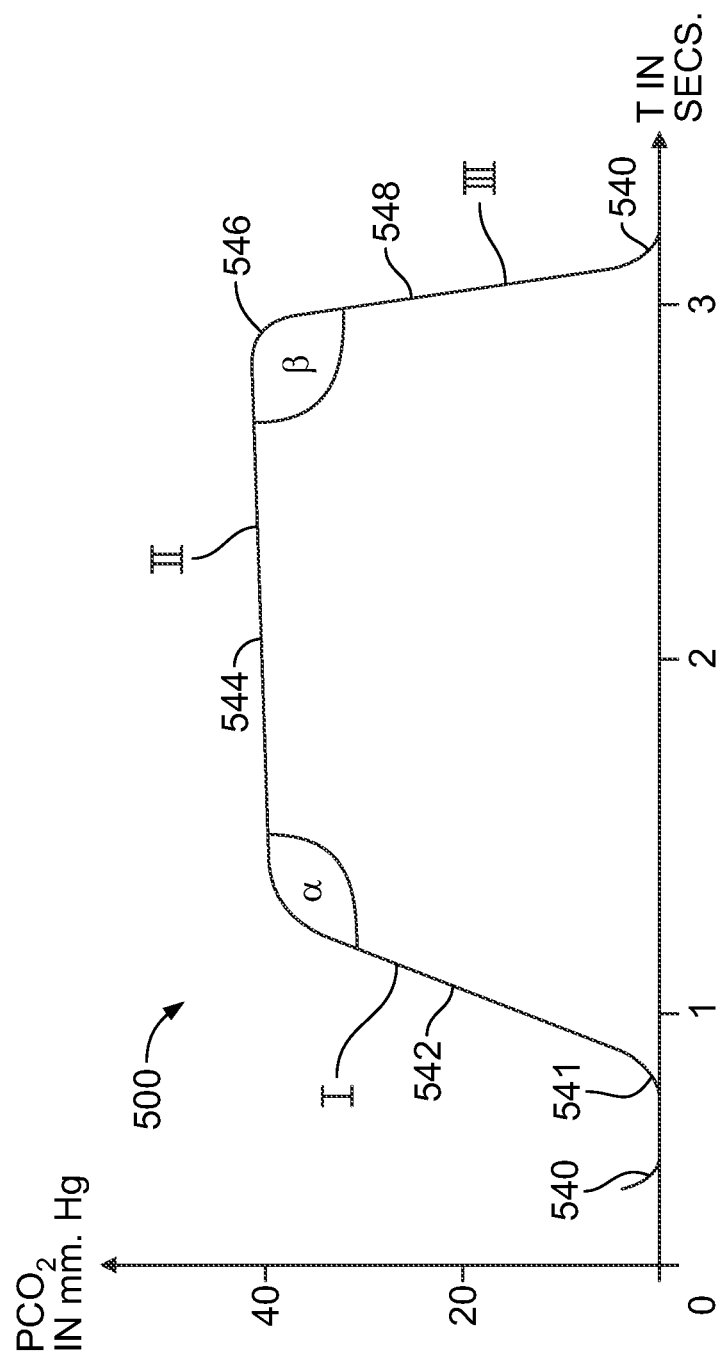
FIG. 5B illustrates a capnograph waveform during normal breathing, according to an embodiment of the present disclosure.

FIG. 5B illustrates a capnograph waveform 500 obtained from a normal healthy subject, according to an embodiment of the present disclosure. During inspiration a baseline 540 shows a close-to-zero value of the partial pressure of carbon dioxide, $PCO_2$, unless partial rebreathing is present. At the commencement of exhalation 541, $PCO_2$ remains close to zero as gas from the anatomical dead space leaves the airway. The capnograph waveform 500 then rises sharply along leg 542 as alveolar gas mixes with dead space gas, until the alveolar plateau 544 is reached. The alveolar plateau 544 is maintained until the end of the exhalation phase, with the value of $PCO_2$ rising gradually during the whole of the plateau, up to the end tidal value ($EtCO_2$) 546. The end tidal value 546 occurs at the onset of the inhalation phase, during which the value of $PCO_2$ shows a sharp fall along leg 548 back to its virtually zero value at the baseline 540. The close-to-zero value of $PCO_2$ at the end of the inspiration phase is known as the fractional inspired value $FiCO_2$.

The angle between the alveolar rise 542 and the alveolar plateau 544 is known as the angle $\alpha$, and is normally in a range between approximately 100° and approximately 110°. The angle $\alpha$ is determined primarily by the V/Q (ventilation/perfusion) status of the lungs. Individuals with obstructions of the airway, such as in the case of chronic obstructive pulmonary disease (COPD) or asthma, have an increased alpha angle. The alpha angle is thus a widely used parameter for a first hand assessment of the patient's overall pulmonary state.

An alternative parameter that may be used for determining the general pulmonary state of the patient is the overall rate of rise of $PCO_2$, which is determined by dividing the maximum value of $PCO_2$ achieved in the waveform, by the time taken from the start of exhalation to the achievement of the maximum value 546 of $PCO_2$. In order to avoid end effects, the 10% and 90% points of the values of $PCO_2$ may be used for the calculation.

The nearly 90° angle between the alveolar plateau 544 and the descending limb 548 of the capnograph waveform 500 is known as the $\beta$ angle. The $\beta$ angle increases as the degree of rebreathing increases. The various parts of the capnographic waveform 500 are known as the phases of the waveform, the alveolar rise phase I, the alveolar plateau phase II, and the inhalation descent, phase III, as indicated in FIG. 5B.

The capnographic sub-system 400 and the capnographic waveform 500 are further described in U.S. Pat. No. 6,428,483, entitled "Waveform Interpreter for Respiratory Analysis," which is hereby incorporated by reference in its entirety. Additionally, the capnographic sub-system 400 may be configured and operate as described in United States Patent Application Publication No. 2011/0066061, entitled "Wireless Capnography," or United States Patent Application Publication No. 2011/0098592, entitled "Methods, Apparatus and Systems for Monitoring CO2," both of which are hereby incorporated by reference in their entireties.

Referring again to FIG. 1, one or more of the PPG sub-system 102, the breath detection sub-system 104, the apnea analysis module 106, and the display 107 may be separate physical components, or one or more of them may be combined together within a workstation, computer, tablet, smartphone, handheld device, integrated housing, monitor, smart cable, adapter, or other hardware component. Such components may include standard computer hardware, such as processors, circuitry, and memory, and may be connected to a display, such as a liquid crystal display (LCD), light-emitting diode (LED) display, touch screen, or other known displays. Connections between the various components may be through wired cables or wireless connections.

The system 100 may include any suitable computer-readable media used for data storage. For example, the apnea analysis module 106 may include computer-readable media. The computer-readable media are configured to store information that may be interpreted by the apnea analysis module 106. The information may be data or may take the form of computer-executable instructions, such as software applications, that cause a microprocessor or other such control unit within the apnea analysis module 106 to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

Figure 6:
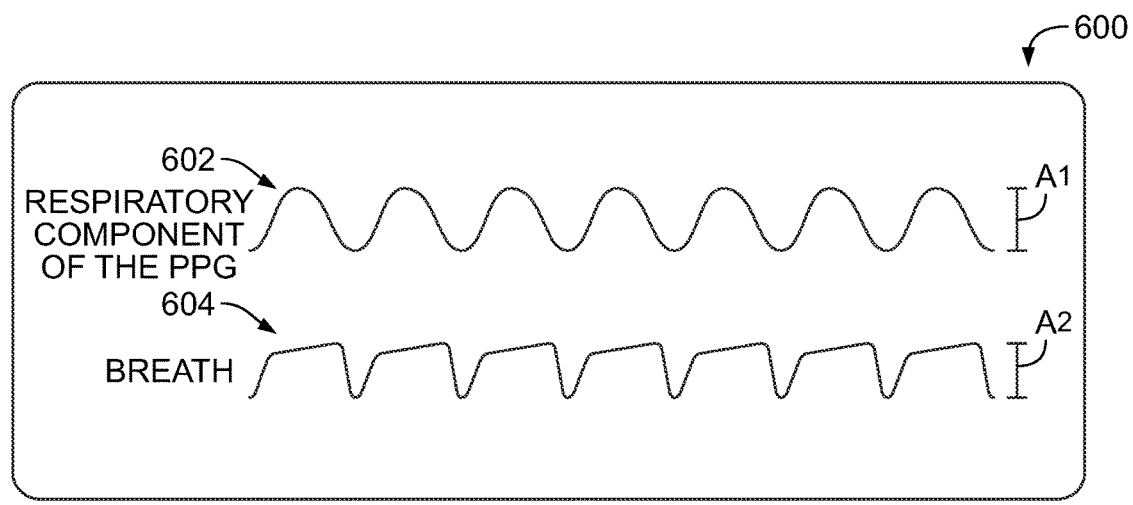
FIG. 6 illustrates a display screen showing a respiratory component of a PPG waveform and a breath waveform during normal breathing, according to an embodiment of the present disclosure.

A display screen 600 of the apnea analysis system according to an embodiment is shown in FIG. 6. The display screen 600 displays the outputs 110 and 108 from the breath-detection and PPG sub-systems, respectively. In an embodiment, the output 108 from the PPG sub-system includes a respiratory component waveform 602 from a PPG signal. The respiratory component waveform 602 represents one or more respiratory components of the PPG signal, as described above with respect to FIGS. 4A-C. In particular, the respiratory component waveform 602 may include the amplitude modulation A, baseline modulation B, or frequency (or duration) modulation F of the PPG, or a combination of these modulations. A combination of the modulations may include an average of one or more of the waveforms, a weighted average, or other combination. The waveforms may be shifted in phase so that they are in phase with each other before averaging. When the respiratory component waveform 602 shows modulations, it may be inferred that the patient is breathing or trying to breathe, and when these modulations disappear from the waveform 602, it may be inferred that the patient has stopped breathing or trying to breathe. Alternatively, the output 108 may be the PPG signal or waveform (such as PPG waveform 10 in FIG. 4B), and the apnea analysis module may derive the respiratory component of the PPG from the PPG signal. In an embodiment, the output 110 from the breath detection system includes a capnographic waveform 604 from a breath signal. When the capnographic waveform 604 shows modulations, it may be inferred that the patient is actually inhaling and exhaling, and when these modulations disappear from the waveform 604, it may be inferred that the patient has stopped breathing. The respiratory component waveform 602 and the breath waveform 604 may be substantially synchronized with one another and displayed over substantially the same time. In another embodiment, the respiration rate signal and/or the respiration effort signal derived from the PPG signal may be displayed as waveforms on the display screen 600, instead of or in addition to the respiratory component waveform 602.

The display 600 shows both the respiratory component waveform 602 and the breath waveform 604. The apnea analysis module compares the two waveforms to determine whether the patient is attempting to breathe and/or breathing normally (non-apneic breathing). In the embodiment of FIG. 6, both the waveforms 602 and 604 indicate normal breathing. The respiratory component waveform 602 includes a modulating segment, and does not include an attenuated segment. The presence of a modulating segment in the respiratory component waveform 602 indicates that the patient's respiration is being detected in the PPG signal, due to one or more modulations of the PPG signal caused by respiration. At a corresponding time, the breath waveform 604 also includes a modulating segment and no attenuated segment, which indicates that $CO_2$ is being detected in the patient's exhalation. The presence of modulating segments in both waveforms indicates that the patient is attempting to breathe and is in fact inhaling and exhaling.

To determine whether the waveforms indicate breathing or attempts to breathe, the apnea analysis module 106 analyzes the waveform to detect the presence of a modulating segment in the waveform. A modulating segment is a segment having portions moving up and down, optionally in a generally repeating or cyclical manner. A modulating segment has fluctuations with a nonzero amplitude. In an embodiment, in order to identify a modulating segment, the apnea analysis module identifies the amplitude of the waveform (such as amplitude A1 or A2 in FIG. 6) and compares it to a range or threshold. A range or threshold of amplitudes for each waveform 602, 604 may be defined as a normal range, indicating normal breathing. If modulations are large enough to give the waveform an amplitude within the defined range, or above the defined threshold, then the apnea analysis module determines that the waveform indicates normal breathing or effort to breathe.

For example, when the respiratory component waveform 602 includes the amplitude, baseline, or frequency modulation waveform, or a combination of these, a lower threshold for the amplitude(s) AMP-A, AMP-B, AMP-F (see FIG. 4C), or a combination of these amplitudes, may be set, and the apnea analysis module 106 calculates the amplitude of the waveform 602 and compares it to the threshold. If the amplitude remains above the threshold, the system determines that the respiratory component of the PPG indicates that the patient is breathing or attempting to breathe. Similarly, a range or threshold may be defined for the breath waveform 604. If the amplitude A2 of the modulations in the breath waveform 604 remain above the threshold, or within a defined normal range, the apnea analysis module determines that the patient is actually breathing. The ranges or thresholds identifying normal breathing and/or regular respiration rate and/or effort in the various signals may be pre-defined and calibrated. As an example, clinical studies of healthy individuals during normal breathing, and/or a patient's particular history of normal breathing, may establish a range of normal breathing, respiration rate, and effort.

In other embodiments, a modulating segment of a waveform may be identified in other ways, such as by assessing the slope and frequency of upstroke portions of the waveform, or by using a Fourier transform method (such as a short-time Fourier transform) or a wavelet method.

As used herein, a flat-line or attenuated segment of a waveform refers to a portion that lacks modulations. An attenuated segment may be flat or substantially flat, exhibit an absence or reduction of modulations, variations, or fluctuations, or have a zero, near-zero, or non-fluctuating first derivative. In an embodiment, an attenuated segment is identified when the amplitude is below the threshold, or outside of the range, that is correlated with normal breathing or a presence of effort to breathe (as discussed above). In another embodiment, an attenuated segment may be identified in relation to a modulating segment. As one example, an attenuated segment may be identified as having a reduced amplitude compared to a segment representative of normal breathing. For example, an attenuated segment may have an amplitude that is 0%-30% of the amplitude of a normal breathing segment. For example, an attenuated segment may be identified as a segment with an amplitude that is below 20%, or below 30%, or below 40% of the amplitude of a normal breathing waveform. An attenuated segment may have an amplitude of modulation that is noticeably different than that of other segments of the waveform that are representative of normal breathing.

Figure 7:
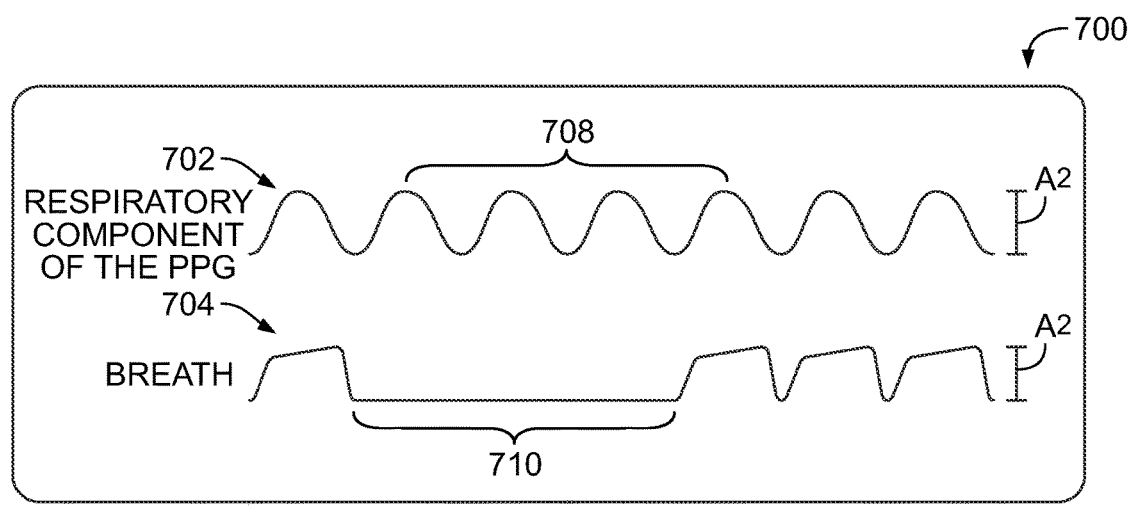
FIG. 7 illustrates a display screen showing a respiratory component of a PPG waveform a breath waveform during an obstructive apnea event, according to an embodiment of the present disclosure.

A display screen 700 according to an embodiment is shown in FIG. 7. In this example, the respiratory component waveform 702 includes a modulating segment 708, and at a corresponding time, the breath waveform 704 includes an attenuated segment 710. The attenuated segment 710 in the breath signal 704 indicates that the breath detection subsystem is not detecting active exhalation from the subject. That is, the subject may not be breathing. However, the respiratory component waveform 702 continues to include modulations in segment 708, induced by respiration. This comparison of the two signals indicates that the patient is attempting to breathe, but is not successfully breathing (for example, is unable to exhale breath). Based on this comparison, the apnea analysis module 106 identifies an apnea event and categorizes it as obstructive apnea.

Still referring to FIG. 7, in an embodiment, the apnea analysis module also checks the $SpO_2$ value of the patient. If the $SpO_2$ value remains high (above a threshold), and does not begin to drop, this indicates that the patient is still receiving oxygen. As a result, based on the absence of breaths in the breath signal (in segment 710), the presence of breaths in the respiratory component of the PPG signal (in segment 708), and the high, stable $SpO_2$ value, the apnea analysis module determines that the breath-sampling interface from the breath detection system is not connected to the patient, and generates a breath sensor-off message or alert.

Still referring to FIG. 7, in an embodiment, the apnea analysis module also monitors the amplitude of the respiratory component waveform 702 for an increase compared to a threshold or historical values (for example, a 20% increase). An increase in the amplitude of the waveform 702 may indicate an increased effort to breathe. If such an increased respiratory effort coincides with the attenuated portion 710 of the breath waveform 704, the apnea analysis module may determine that obstructive apnea is present due to the patient's increased effort to breathe, and no successful breath. The apnea analysis module may then activate an alert or alarm display, message, or sound.

Figure 8:
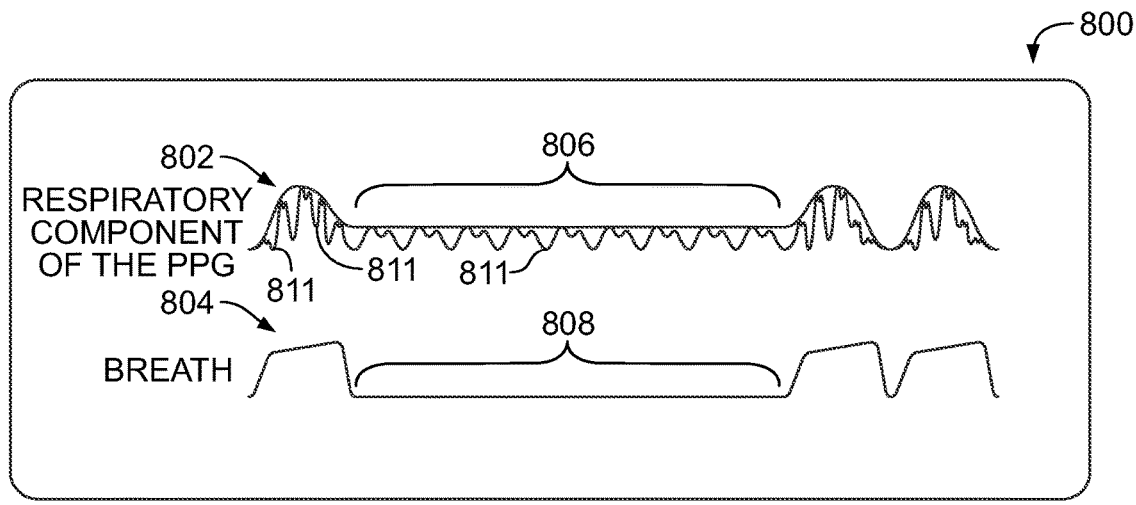
FIG. 8 illustrates a display screen showing a respiratory component of a PPG waveform a breath waveform during a central apnea event, according to an embodiment of the present disclosure.

A display screen 800 according to an embodiment is shown in FIG. 8. In this example, the respiratory component waveform 802 and the breath waveform 804 both include attenuated segments 806 and 808, respectively, at a corresponding time. The attenuated segment 806 in the respiratory component waveform 802 indicates that the PPG signal is no longer exhibiting modulations due to respiration. This indicates that the patient is no longer attempting to breathe. The attenuated segment 808 in the breath waveform 804 indicates that the breath detection system is no longer detecting exhaled $CO_2$ from the patient. This indicates that the patient is no longer breathing. Based on this comparison of the outputs from the two sub-systems, the apnea analysis module identifies an apnea event and categorizes it as central apnea.

In an embodiment, the apnea analysis module also checks the PPG signal for the presence of cardiac pulses 811. If cardiac pulses 811 continue to be present in the PPG signal, then the system determines that the PPG sensor is still properly positioned on the patient, and thus the attenuated segment 806 is likely due to apnea rather than a sensor-off condition. While not shown in FIGS. 6 and 7, the display screens 600 and 700 may also display the pulsatile component of the PPG waveform, such as shown in FIGS. 8 and 9.

Figure 9:
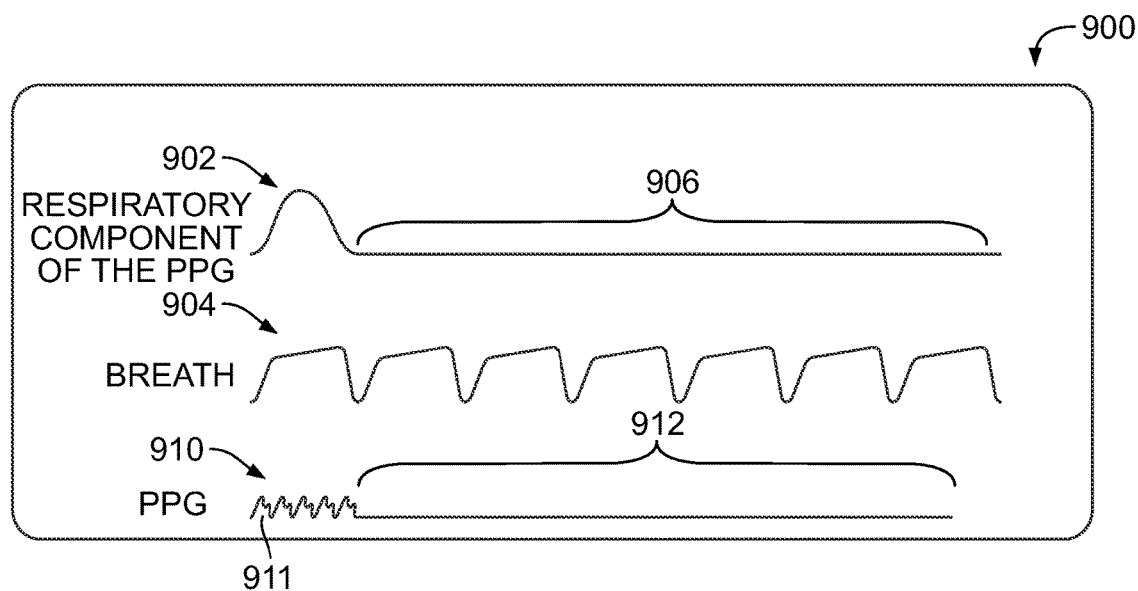
FIG. 9 illustrates a display screen showing a respiratory component of a PPG waveform and a breath waveform during a PPG probe-off event, according to an embodiment of the present disclosure.

A display screen 900 according to an embodiment is shown in FIG. 9. In this example, the apnea analysis system determines that the PPG sensor is not properly positioned on the patient. The respiratory component waveform 902 includes an attenuated segment 906, while at a corresponding time, the breath waveform 904 includes a modulating segment. Additionally, the PPG waveform 910 includes an attenuated segment 912, devoid of cardiac pulses 911. Because the breath waveform indicates that the patient is still successfully breathing, the lack of both cardiac and respiratory modulations in the PPG signal indicates that the sensor has fallen off the patient, rather than indicating that cardiac and respiratory activity has stopped. Accordingly, the apnea analysis module 106 displays a PPG sensor-off alert or message on the display 107.

In an embodiment, the apnea analysis module 106 is able to identify and classify a type of apnea based on a comparison of the respiratory component of the PPG waveform with the breath waveform. In various embodiments, the apnea analysis module may also consider the PPG waveform, $SpO_2$ value, respiration effort, and/or other inputs. The apnea analysis module may accomplish this comparison by referring to a logic table, as described below.

FIG. 10 illustrates a logic table 1000 that may be used with an apnea analysis system and method, according to an embodiment of the present disclosure. The table 1000 includes a breath waveform column 1002, an $SPO_2$ column 1004, a respiration column 1006, a respiratory effort column 1008, and a condition column 1010. The logic shown in the table 1000 may be used by the apnea analysis module 106 shown in FIG. 1.

The breath waveform column 1002 indicates a presence or absence of exhaled breath, as determined from the output 110 from the breath detection system.

The $SpO_2$ column includes an $SpO_2$ value, as determined from the PPG signal, or an indication of whether the $SpO_2$ value is within a range or above or below a threshold. The $SPO_2$ value may be used as a further analytical tool for apnea analysis. If an individual is breathing, oxygen is provided to the blood, and the oxygen saturation value remains at a normal level. An oxygen saturation level may be chosen as a threshold for apnea detection. For example, in an embodiment, the threshold is 85%. However various other $SPO_2$ levels may be used. For example, the threshold may be 80%, 90%, or 95%. As discussed further below, the oxygen saturation value, and in particular whether it is above or below a designated threshold, may be used as one of several input factors to determine whether the patient is breathing normally.

The respiration column 1006 includes an indication of the presence or absence of respiration from a respiratory component of the PPG signal.

The respiratory effort column indicates a normal, high, or diminished respiratory effort, as determined from a respiratory component of the PPG signal. A "normal" respiratory effort may be determined by a physician, clinician, or the like. For example, the user may set a normal respiratory effort as between a particular low threshold percentage and a particular high percentage in relation to a calibrated PPG waveform. As an example, normal respiratory effort may be between 50% and 150% of a pre-calibrated normal respiratory effort signal derived from the PPG signal 108. As another example, respiratory effort may be identified as high based on an increase in amplitude of the respiratory component of the PPG as compared to a baseline. However, the normal respiratory effort may be between percentages that are greater or less than those noted.

Referring to FIG. 10, the first row of the logic table indicates breaths present, $SpO_2$ above a specified threshold, respiration present, and respiration effort normal. Based on these inputs, the apnea analysis module determines that the individual is breathing normally, that is, regular respiration.

The second row of the logic table indicates that breaths are absent, $SpO_2$ is above the threshold, respiration is not detected from the PPG waveform, and respiration effort is not detected. Based on these inputs, the apnea analysis module 106 determines the existence of an initial stage of central apnea. The initial stage of central apnea may become a long term central event or transition into a mixed apnea. In such a scenario, the apnea analysis module 106 may generate an alarm.

The third row of the logic table indicates that breaths are absent, the $SpO_2$ value is below the threshold (or the $SpO_2$ value is dropping and the rate of change of the $SpO_2$ value is above a threshold, indicating a rapid drop), and respiration and respiratory effort are not detected. Based on these inputs, the apnea analysis module 106 determines the existence of a long term or severe central apnea. Accordingly, the apnea analysis module 106 may generate a corresponding alarm. The alarm for the long term or severe central apnea may be more urgent than that for the initial stage of central apnea. For example, the alarm may be louder and/or a different color or flashing, as compared to the alarm for the initial stage of central apnea. As such, the apnea analysis module 106 may differentiate alarms based on the severity of the apnea that is detected.

Still referring to FIG. 10, in the fourth row, breaths are absent, $SpO_2$ is above the threshold, and respiration is present, but a respiratory effort is high. Based on these inputs, the apnea analysis module 106 determines that obstructive apnea is present. As such, the apnea analysis module 106 may generate an appropriate alarm indicating obstructive apnea.

In the fifth row of the logic table 1000, breaths are absent, the $SpO_2$ level is above a threshold, respiration is present, and respiratory effort is normal. Based on these inputs, the apnea analysis module 106 may determine that the breath sensor or probe is disconnected (e.g., a "probe off" condition), and generate an appropriate alarm or notification.

Finally, in the last row of the logic table 1000, breaths are intermittent or cycling between being present and absent, the $SpO_2$ value is under a threshold or fluctuating markedly, and respiration and respiratory effort are intermittent or cycling. Based on these inputs, the apnea analysis module determines the presence of apnea, and identifies the apnea as a mixed apnea. The module may provide an alarm, and may increase the severity of the alarm if the apnea event continues.

Figure 11:
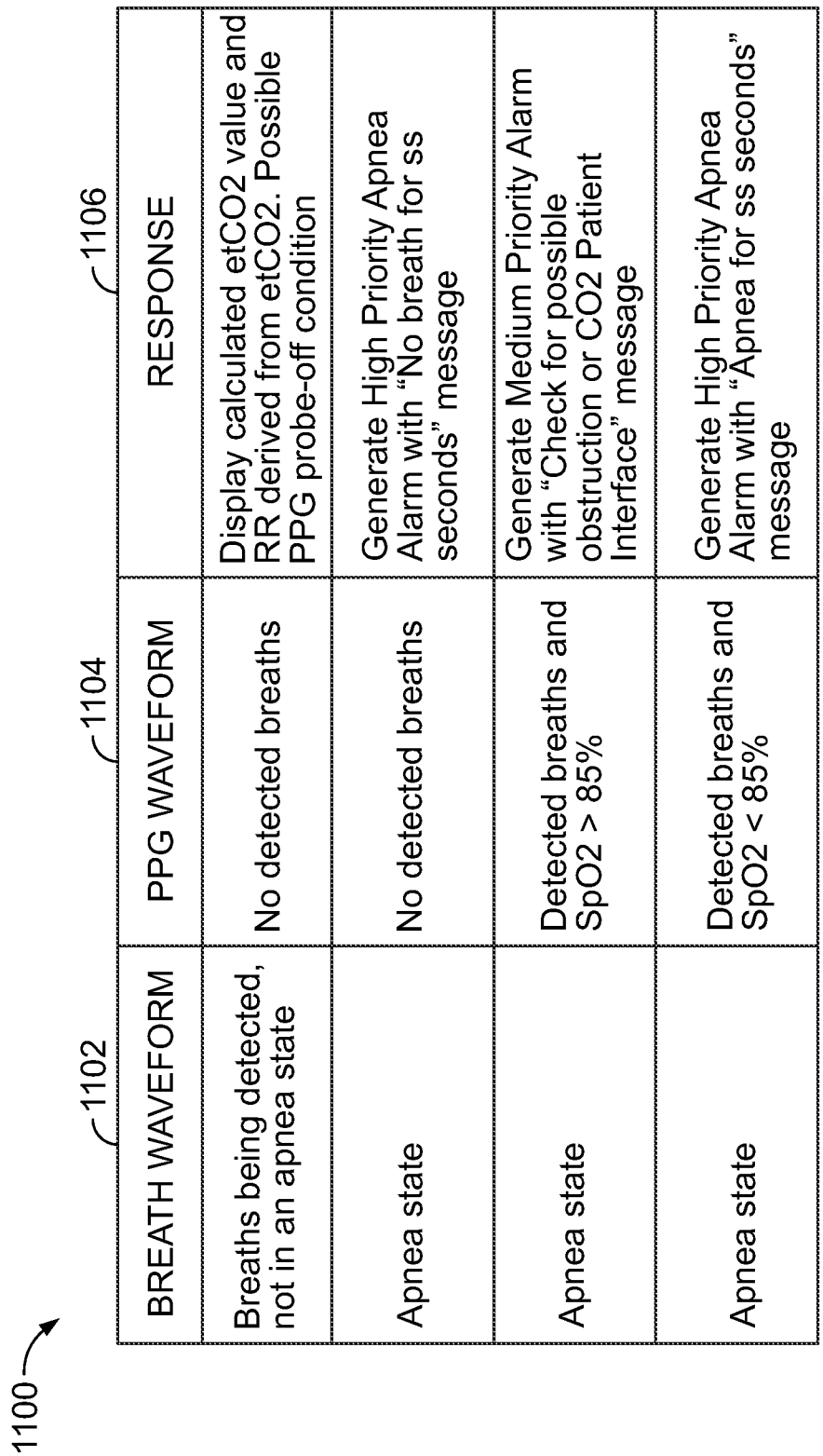
FIG. 11 illustrates a logic table that may be used with an apnea analysis system and method, according to an embodiment of the present disclosure.

FIG. 11 illustrates a logic table 1100 that may be used with an apnea analysis system and method, according to an embodiment of the present disclosure. The table 1100 includes a breath waveform column 1102, a PPG waveform column 1104, and a response column 1106. The logic shown in the table 1100 may be used by the apnea analysis module 106 shown in FIG. 1.

In the first row of the logic table 1100, breaths are detected in the breath waveform, but not in the PPG waveform (such as through a lack of respiration rate and respiratory effort). Based on these inputs, the apnea analysis module 106 may determine that the PPG sensor is disconnected from the patient. The apnea analysis module may display the exhaled $CO_2$ and the respiration rate values derived from the breath waveform, and generate an appropriate sensor-off alarm.

In the second row of the logic table 1100, breaths are absent from the breath output 110 and the PPG output 108. Based on these inputs, the apnea analysis module 106 may generate a high priority apnea alarm. The apnea alarm may indicate central apnea and may include a message stating "no breath for ss seconds," in which "ss" is a particular number of seconds since the last detected breath.

In the third row, breaths are absent from the breath output 110, but the PPG sub-system 102 provides a PPG output 108 in which the $SPO_2$ level is above a threshold (such as 85%), and breaths are detected (such as from one or more respiratory components of the waveform). Based on these inputs, the apnea analysis module determines that the breath detection sensor is not properly positioned. No breaths are detected, but the $SpO_2$ level remains above a threshold, which indicates that the patient is continuing to receive oxygen. As a result, the system generates a medium priority alarm, which may recite, for example, "check for possible obstruction or $CO_2$ patient interface." As an example, the patient interface may be nasal prongs or a face mask of a mainstream or sidestream breath sampling device of a capnographic sub-system.

Still referring to FIG. 11, in the fourth row, breaths are absent from the breath output 110, and the PPG sub-system 102 generates a signal indicating that the $SPO_2$ level is below a threshold (such as 85%) and breathing effort is present. Based on these inputs, the apnea analysis module 106 may determine an obstructive apnea event, and may generate a high priority alarm, which may recite, for example, "apnea for ss seconds."

Figure 12:
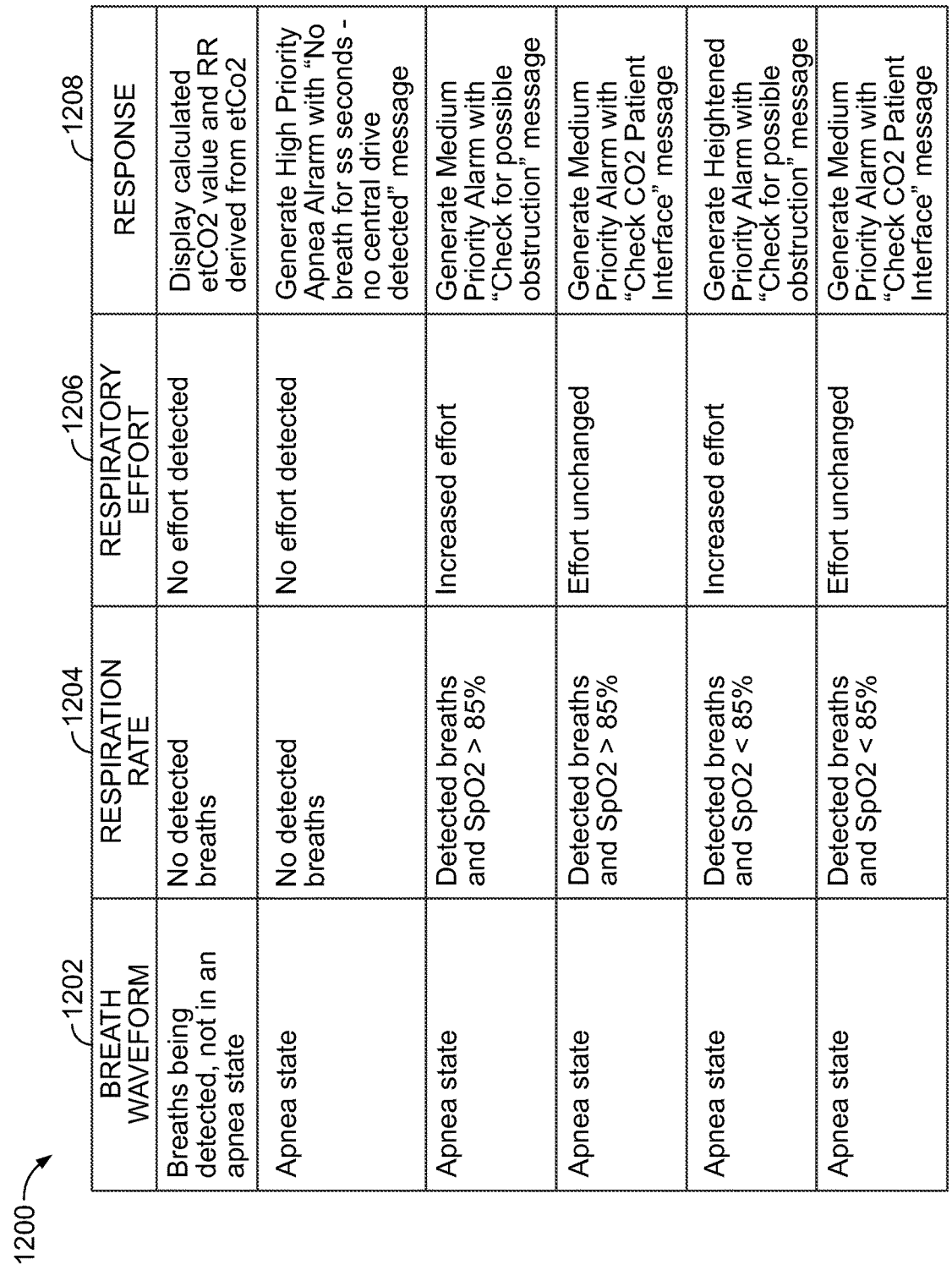
FIG. 12 illustrates a logic table that may be used with an apnea analysis system and method, according to an embodiment of the present disclosure.

FIG. 12 illustrates a logic table 1200 that may be used with an apnea analysis system and method, according to an embodiment of the present disclosure. The table 1200 includes a breath waveform column 1202, a respiration rate column 1204, a respiratory effort column 1206, and a response column 1208. In an embodiment, the respiration rate and effort columns are derived from a respiratory component of the PPG waveform. The logic shown in the table 1200 may be used by the apnea analysis module 106 shown in FIG. 1.

In the first row of the table 1200, breaths are present in the breath waveform, but respiratory rate and effort are absent from the PPG waveform. Based on these inputs, the apnea analysis module 106 displays the calculated signals derived from the breath waveform, and determines that the PPG sensor is disconnected from the patient. The module may also generate an appropriate alarm.

In the second row of table 1200, no breaths are detected by the breath detection sub-system, and the PPG sub-system 102 is not detecting a respiration rate or respiratory effort. Based on these inputs, the apnea analysis module 106 may generate a high priority apnea alarm identifying central apnea.

In the third row of table 1200, no breaths are detected by the breath detection sub-system, and the PPG sub-system 102 detects a respiration rate, an $SPO_2$ level above a threshold (such as 85%), and an increased respiratory effort. Based on these inputs, the apnea analysis module 106 identifies a possible obstructive apnea condition and generates a medium priority alarm, such as "check for possible obstruction." In the fifth row, based on the same inputs but a decreasing $SpO_2$, the apnea analysis module 106 identifies an obstructive apnea condition and generates a heightened priority alarm, such as "check for possible obstruction" as well as an alert regarding a low or dropping $SPO_2$ level.

In the fourth row, the respiratory effort is unchanged, instead of increased, and the $SpO_2$ level is above a threshold. Based on these inputs, the apnea analysis module 106 determines that the breath interface is no longer connected to the patient, and generates a medium priority alarm, such as "check breath interface." That is, when the PPG sub-system 102 detects otherwise normal breathing, but the breath detection sub-system 104 does not detect breath, then the apnea analysis module 106 may determine that a breath interface, such as a sampling tube, is no longer operatively connected to an individual. In the sixth row, based on the same inputs but a decreasing $SpO_2$, the apnea analysis module 106 generates a medium priority alarm, such as "check breath interface."

As shown in FIGS. 10-12, for example, the apnea analysis module 106 may generate various alarms of increasing priority depending on the nature of the breathing status of the individual. The alarms may be tiered based on the type of condition detected. For example, the apnea analysis module 106 may generate a highest urgency alarm when central apnea is detected and correlated with an $SPO_2$ level below a threshold. The highest urgency alarm may be associated with flashing colors and an audio signal (such as beep or buzz or other alarm) at the highest volume. Obstructive apnea may cause the apnea analysis module 106 to generate a high priority alert, which may be defined by flashing text on a screen, and/or an audio signal of increasing volume. A probe or interface off condition may cause the apnea analysis module 106 to generate a medium priority alert, which may be defined by text on a screen, and/or an audio signal.

Referring again to FIG. 1, the apnea analysis module 106 may determine and classify apnea by comparing a respiratory component of the PPG signal or output 108 with the breath signal or output 110, such as a capnograph breath waveform. The apnea analysis module 106 may use probability density estimates calculated, for example, using non-parametric Bayesian estimates, neural networks, or any suitable method of hetero-associative function estimation to determine the respiratory status (for example, normal breathing, central apnea, obstructive apnea, or mixed apnea) of the individual. Alternatively, the apnea analysis module 106 may employ rule based systems and adaptive rule based systems such as propositional logic, predicate calculus, and/or modal, non-monotonic or fuzzy logics, for example.

Alternatively, the apnea analysis module 106 may use logic tables, as described above.

The apnea analysis module 106 may determine that the individual is experiencing mixed apnea if episodes of obstructive and central apnea occur within a predetermined period of time. For example, if obstructive apnea and central apnea are detected within one minute of each other, the apnea analysis module 106 may determine that the individual is experiencing mixed apnea. In other embodiments, the time window for determination of mixed apnea may be greater or less than one minute, such as, for example, 30, 40, 50, 70, 80, 90, or 120 seconds.

Figure 13:
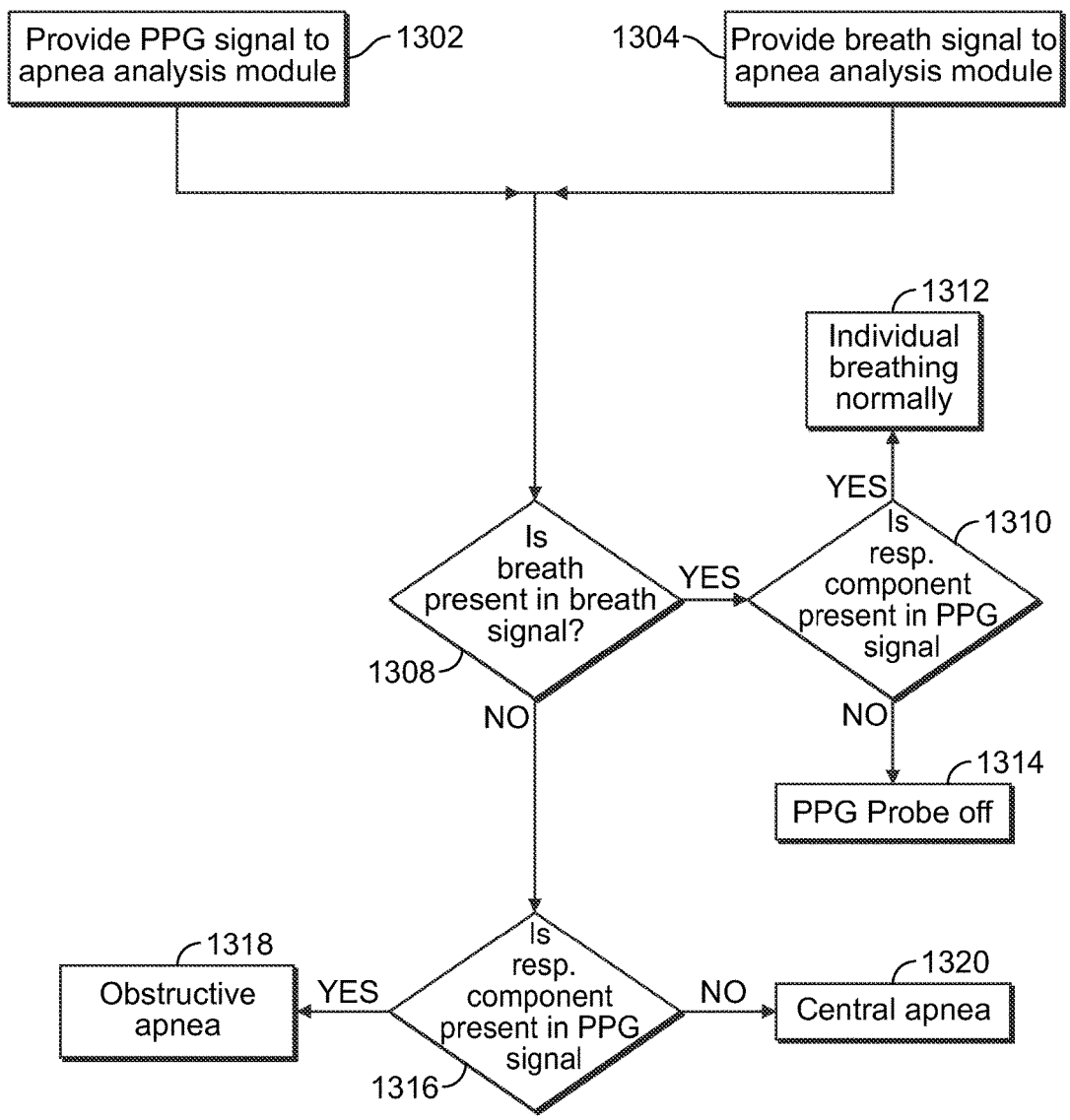
FIG. 13 illustrates a flow chart of a method of operating an apnea analysis system, according to an embodiment of the present disclosure.

FIG. 13 illustrates a flow chart of a method of operating an apnea analysis system, according to an embodiment of the present disclosure. At 1302, a PPG signal is provided to an apnea analysis module. For example, a PPG sub-system, such as a pulse oximeter, may provide a PPG signal in the form of a PPG waveform to the apnea analysis module. Optionally, the PPG sub-system may provide a respiratory component of the PPG signal to the apnea analysis module. At 1304, a breath signal is provided to the apnea analysis module. For example, a capnographic sub-system may provide a breath signal in the form of a capnographic waveform to the apnea analysis module.

At 1308, it is determined whether a breath is present in the breath signal. If breath is present, the process continues to 1310, where it is determined whether a respiratory component (such as a baseline modulation, amplitude modulation, frequency modulation, or calculated parameter such as respiration rate and/or respiratory effort), is present in the PPG signal at a corresponding time. If a respiratory component is present, the process continues to 1312, where it is determined that the individual is breathing normally. If a respiratory component is not present, the process continues to 1314, where a PPG probe-off condition is signaled.

If, however, breath is not present at 1308, the process continues to 1316, where it is determined whether a respiratory component is present in the PPG signal at a corresponding time. If the respiratory component is present, then the process continues to 1318, where it is determined that the individual is experiencing obstructive apnea. If, however, the respiratory component is not present, then the process continues to 1320, where it is determined that the individual is experiencing central apnea.

Embodiments of the present disclosure provide systems and methods of detecting and classifying apnea events as central, obstructive, or mixed, for example, based on a reduction in a breath signal or respiratory signal, and a corresponding status of the other signal. Determining the type of apnea guides appropriate and timely medical interventions.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet.

The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "module."

The computer or processor executes a set of instructions that are stored in one or more storage elements, in order to process data. The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The block diagrams of embodiments herein illustrate one or more modules. It is to be understood that the modules represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory.

It is to be understood that the above description is intended to be illustrative, and not restrictive. For example, the above-described embodiments (and/or aspects thereof) may be used in combination with each other. In addition, many modifications may be made to adapt a particular situation or material to the teachings without departing from its scope. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An apnea analysis method comprising:
   receiving, using an apnea analysis system, a photoplethysmographic (PPG) signal indicative of a cardiac status of an individual from a PPG sensor;
   receiving, using the apnea analysis system, a breath signal indicative of a breathing status of the individual from a breath sensor;
   identifying, using the apnea analysis system, a respiratory component of the PPG signal indicative of a respiration effort or a respiration rate;
   calculating, using the apnea analysis system, an oxygen saturation value indicative of oxygen saturation of the individual based on the PPG signal;
   identifying, using the apnea analysis system, a presence of apnea based on at least one of the breath signal, the respiratory component of the PPG signal, and the oxygen saturation value;
   differentiating, using the apnea analysis system, between obstructive apnea and central apnea, based on the breath signal, the respiratory component of the PPG signal, and the oxygen saturation value; and
   providing, using the apnea analysis system, an indication based on the differentiating.

2. The method of claim 1, further comprising outputting a confidence metric with respect to the respiratory component of the PPG signal based on detected modulations of a baseline, a cardiac pulse amplitude, or a cardiac pulse frequency.

3. The method of claim 1, further comprising identifying a presence of normal breathing when the breath signal and the respiratory component of the PPG signal each include a modulating segment.

4. The method of claim 1, wherein identifying the presence of apnea comprises identifying an attenuation of the breath signal, or identifying an attenuation of the respiratory component of the PPG signal, or identifying attenuations of both.

5. The method of claim 4, wherein differentiating comprises identifying obstructive apnea when the respiratory component of the PPG includes a modulating segment and the breath signal includes the attenuation.

6. The method of claim 4, wherein differentiating comprises identifying central apnea when attenuations are identified in both the breath signal and the respiratory component of the PPG signal.

7. The method of claim 4, wherein the respiratory component of the PPG signal comprises a modulation of a baseline of the PPG signal.

8. The method of claim 4, wherein the respiratory component of the PPG signal comprises a modulation of an amplitude of cardiac pulses in the PPG signal.

9. The method of claim 4, wherein the respiratory component of the PPG signal comprises a modulation of a frequency of cardiac pulses in the PPG signal.

10. The method of claim 1, wherein the breath sensor is a gas analyzer configured to analyze $CO_2$ content of the individual's breath.

11. The method of claim 1, further comprising:
    differentiating, using the apnea analysis system, between initial stages of central apnea and longer term or more severe central apnea based on the oxygen saturation value.

12. The method of claim 1, further comprising:
    determining, using the apnea analysis system, a respiration value indicative of presence or absence of the individual's respiration based on the PPG signal; and
    wherein differentiating between obstructive apnea and central apnea is based on the respiration value.

* * * * *